(12) United States Patent
Conlon et al.

(10) Patent No.: US 11,577,033 B2
(45) Date of Patent: Feb. 14, 2023

(54) VALVED SPACER FOR INHALATION DEVICE

(71) Applicant: Medline Industries, LP, Springfield, IL (US)

(72) Inventors: Colin Conlon, Dublin (IE); Prashant S. Nagathan, Cary, NC (US); Michael Stephen Hill, Raleigh, NC (US); Olaf Lally, County Longford (IE); James Lorek, Cary, NC (US)

(73) Assignee: Medline Industries, LP, Springfield, IL (US)

( * ) Notice: Subject to any disclaimer, the term of this patent is extended or adjusted under 35 U.S.C. 154(b) by 463 days.

(21) Appl. No.: 16/431,850

(22) Filed: Jun. 5, 2019

(65) Prior Publication Data
US 2019/0366018 A1 Dec. 5, 2019

Related U.S. Application Data

(60) Provisional application No. 62/680,923, filed on Jun. 5, 2018.

(51) Int. Cl.
*A61M 15/00* (2006.01)

(52) U.S. Cl.
CPC ........ *A61M 15/002* (2014.02); *A61M 15/009* (2013.01); *A61M 15/0016* (2014.02); *A61M 15/0018* (2014.02); *A61M 15/0021* (2014.02); *A61M 2205/581* (2013.01); *A61M 2205/583* (2013.01)

(58) Field of Classification Search
CPC ............ A61M 15/002; A61M 15/0016; A61M 15/0018; A61M 15/0021; A61M 15/009; A61M 2205/581; A61M 2205/582
See application file for complete search history.

(56) References Cited

U.S. PATENT DOCUMENTS

| 3,837,341 A | 9/1974 | Bell |
| 4,470,412 A | 9/1984 | Nowacki et al. |
| 4,534,343 A | 8/1985 | Nowacki et al. |
| 4,852,561 A | 8/1989 | Sperry |
| 5,012,803 A | 5/1991 | Foley et al. |

(Continued)

FOREIGN PATENT DOCUMENTS

| WO | 2017011865 A1 | 1/2017 |
| WO | 2017140599 A1 | 8/2017 |

OTHER PUBLICATIONS

International Search Report and Written Opinion issued in PCT/US19/35507, dated Aug. 28, 2019.

*Primary Examiner* — Timothy A Stanis
(74) *Attorney, Agent, or Firm* — Quarles & Brady LLP

(57) ABSTRACT

An aerosol inhalation spacer for use with a metered-dose inhaler canister is disclosed. The spacer includes a transparent chamber housing having a body with an input end and an output end and defining an interior space. A mouthpiece is connected to the output end of the chamber housing. An inhaler adapter is connected to the input end of the chamber housing. A valve member is disposed between the mouthpiece and the output end of the chamber housing, the valve member includes a one-way inhalation valve and a one-way exhalation valve. A flow indicator is connected to the inhaler adapter and extends into the interior space of the chamber housing for indicating an inhalation flow rate to the user.

17 Claims, 19 Drawing Sheets

(56) References Cited

U.S. PATENT DOCUMENTS

| | | | |
|---|---|---|---|
| 5,012,804 A | 5/1991 | Foley et al. | |
| 5,042,467 A | 8/1991 | Foley | |
| 5,385,140 A * | 1/1995 | Smith | A61M 15/0086 |
| | | | 128/200.23 |
| 5,427,089 A | 6/1995 | Kraemer | |
| 5,522,380 A | 6/1996 | Dwork | |
| 5,584,285 A | 12/1996 | Salter et al. | |
| 5,598,835 A | 2/1997 | von Schrader | |
| 5,724,962 A | 3/1998 | Vidgren et al. | |
| 5,816,240 A | 10/1998 | Komesaroff | |
| 5,842,468 A | 12/1998 | Denyer et al. | |
| 5,848,588 A | 12/1998 | Foley et al. | |
| 5,881,718 A | 3/1999 | Mortensen et al. | |
| 6,026,807 A * | 2/2000 | Puderbaugh | A61M 15/0086 |
| | | | 128/200.14 |
| 6,039,042 A | 3/2000 | Sladek | |
| 6,176,234 B1 | 1/2001 | Salter et al. | |
| 6,176,237 B1 | 1/2001 | Wunderlich et al. | |
| 6,202,643 B1 | 3/2001 | Sladek | |
| 6,240,917 B1 | 6/2001 | Andrade | |
| 6,257,231 B1 | 7/2001 | Shick et al. | |
| 6,293,279 B1 | 9/2001 | Schmidt et al. | |
| 6,345,617 B1 | 2/2002 | Engelbreth et al. | |
| 6,363,932 B1 | 4/2002 | Forchione et al. | |
| 6,435,177 B1 | 8/2002 | Schmidt et al. | |
| 6,539,939 B2 | 4/2003 | Rubin | |
| 6,557,549 B2 | 5/2003 | Schmidt et al. | |
| 6,578,571 B1 | 6/2003 | Watt | |
| 6,606,990 B2 | 8/2003 | Stapleton et al. | |
| 6,615,826 B1 | 9/2003 | Gabrio et al. | |
| 6,681,768 B2 | 1/2004 | Haaije de Boer et al. | |
| 6,698,422 B2 | 3/2004 | Fugelsang et al. | |
| 6,712,070 B2 | 3/2004 | Drachmann et al. | |
| 6,848,443 B2 | 2/2005 | Schmidt et al. | |
| 6,904,908 B2 * | 6/2005 | Bruce | A61M 16/14 |
| | | | 128/200.23 |
| 6,932,082 B2 | 8/2005 | Stein | |
| 6,962,151 B1 | 11/2005 | Knoch et al. | |
| 7,013,896 B2 | 3/2006 | Schmidt | |
| 7,107,987 B2 | 9/2006 | Sundaram et al. | |
| 7,131,440 B2 | 11/2006 | Sonntag | |
| 7,178,518 B2 | 2/2007 | Watt et al. | |
| 7,201,164 B2 | 4/2007 | Grychowski et al. | |
| 7,201,165 B2 | 4/2007 | Bruce et al. | |
| 7,360,537 B2 | 4/2008 | Snyder et al. | |
| 7,418,962 B1 | 9/2008 | Rao | |
| 7,562,656 B2 | 7/2009 | Gallem et al. | |
| 7,686,016 B2 | 3/2010 | Wharton et al. | |
| 7,748,385 B2 * | 7/2010 | Lieberman | A61M 15/0018 |
| | | | 128/207.12 |
| 7,849,853 B2 | 12/2010 | Grychowski et al. | |
| 8,061,352 B2 | 11/2011 | Grychowski et al. | |
| 8,074,641 B2 | 12/2011 | Gallem et al. | |
| 8,074,642 B2 | 12/2011 | Bruce et al. | |
| RE43,174 E | 2/2012 | Schmidt et al. | |
| 8,151,794 B2 | 4/2012 | Meyer et al. | |
| 8,459,252 B2 | 6/2013 | Gallem et al. | |
| 8,550,067 B2 | 10/2013 | Bruce et al. | |
| 8,770,188 B2 * | 7/2014 | Stenzler | A61M 15/0086 |
| | | | 128/200.23 |
| RE45,068 E | 8/2014 | Schmidt et al. | |
| 8,875,697 B2 | 11/2014 | Denyer et al. | |
| 8,875,706 B2 | 11/2014 | Meyer et al. | |
| 8,905,020 B2 | 12/2014 | Eagle | |
| 8,910,625 B2 | 12/2014 | Mullinger et al. | |
| 8,973,571 B1 | 3/2015 | Gallem et al. | |
| 9,308,335 B2 | 4/2016 | Gallem et al. | |
| 9,352,107 B2 | 5/2016 | Von Hollen et al. | |
| 9,364,621 B2 | 6/2016 | Von Hollen et al. | |
| 9,364,622 B2 | 6/2016 | Steelman et al. | |
| RE46,050 E | 7/2016 | Schmidt et al. | |
| 9,517,315 B2 | 12/2016 | Meyer et al. | |
| 9,555,202 B2 | 1/2017 | Von Hollen et al. | |
| 9,642,980 B2 | 5/2017 | Alizoti et al. | |
| 9,649,455 B2 | 5/2017 | Blacker et al. | |
| 9,700,688 B2 | 7/2017 | Engelbreth et al. | |
| 9,700,689 B2 | 7/2017 | Bruce et al. | |
| 9,814,849 B2 | 11/2017 | Bruce et al. | |
| 9,950,128 B2 | 4/2018 | Meyer et al. | |
| 2007/0074718 A1 | 4/2007 | Austin | |
| 2009/0013993 A1 | 1/2009 | Bird et al. | |
| 2011/0232636 A1 | 9/2011 | Von Hollen et al. | |
| 2012/0318261 A1 | 12/2012 | Newhouse et al. | |
| 2013/0186393 A1 | 7/2013 | Von Hollen et al. | |
| 2013/0199520 A1 * | 8/2013 | Dhuper | A61M 16/127 |
| | | | 128/205.24 |
| 2015/0047635 A1 | 2/2015 | Poree | |
| 2016/0256641 A1 | 9/2016 | Lisberg | |
| 2016/0339187 A1 | 11/2016 | Smaldone | |
| 2017/0028161 A1 | 2/2017 | Meyer et al. | |
| 2017/0232212 A1 | 8/2017 | Bruin et al. | |
| 2017/0252524 A1 | 9/2017 | Kruger | |
| 2017/0296772 A1 | 10/2017 | Costella et al. | |
| 2017/0333645 A1 * | 11/2017 | Alizoti | A61B 5/087 |

* cited by examiner

VALVED SPACER FOR INHALATION DEVICE

CROSS-REFERENCE TO RELATED APPLICATIONS

This application claims the benefit of priority to U.S. Provisional Patent Application No. 62/680,923 filed Jun. 5, 2018, the content of which is incorporated herein by reference in its entirety.

TECHNICAL FIELD

The present disclosure generally relates to an aerosol inhalation device, and more particularly, to a valved spacer for a metered-dose inhaler.

BACKGROUND

Patients with asthma and other lung conditions are frequently prescribed medication that is delivered straight to their lungs as aerosol via a metered-dose inhaler (MDI). Patients who have trouble breathing may use a spacer device in combination with an MDI to help them inhale the aerosolized medication more easily and effectively. For instance, if a patient does not use a proper inhalation technique with a MDI then the desired dose of medication may not reach the lungs. Such patients who cannot properly inhale medication directly from an MDI typically benefit from adding a spacer, which is a type of holding chamber that attaches to the inhaler and slows the delivery of medication.

Conventional spacers make inhalers easier to use and deliver medication more efficiently. However, problems with existing spacers often make it difficult for the patient to inhale the medication into their lungs and subsequently exhale so that the patient can be ready to breathe in additional medication as necessary. Furthermore, the effectiveness of delivery of aerosolized medication to a patient's lungs may be diminished when the patient cannot gauge the timing and speed of their own breathing relative to the activation of the inhaler. This problem is especially apparent when the patient is critically ill and/or very weak and is already having extreme difficulties in breathing. Moreover, since several breaths are often required for an administration of the required drug dosage, conventional spacers that inhibit the flow of exhaled breaths can make it quite difficult for the user to exhale, thus impacting the effectiveness of subsequent inhaled breaths of medication. Therefore, there is a need for an aerosol inhalation device that overcomes these problems as well as many other problems of conventional spacers.

SUMMARY

The foregoing needs are met by implementations of an aerosol inhalation device for use with a metered-dose inhaler according to the present disclosure. According to one aspect of the disclosure, an aerosol inhalation spacer for use with a metered-dose inhaler comprises a transparent chamber housing having a body with an input end and an output end and defining an interior space; a mouthpiece connected to the output end of the chamber housing; an inhaler adapter connected to the input end of the chamber housing; and a valve member disposed between the mouthpiece and the output end of the chamber housing, the valve member adapted to cooperate with a portion of the chamber housing to form a one-way inhalation valve and a one-way exhalation valve; the one-way inhalation valve configured to allow a flow of aerosol to pass from the interior space of the chamber housing to the mouthpiece but not to the atmosphere during inhalation, and the one-way exhalation valve configured to allow a flow of exhaled air to pass from the mouthpiece to the atmosphere but not to the interior space of the chamber housing during exhalation.

According to another aspect of the disclosure, the output end of the holding chamber further comprises a flow control member adapted to cooperate with the valve member to form the inhalation and exhalation valves.

According to another aspect of the disclosure, the inhalation valve comprises a one-way inhalation flap valve.

According to another aspect of the disclosure, the exhalation valve comprises a one-way exhalation flap valve.

According to another aspect of the disclosure, the exhalation valve and the chamber housing are configured to direct exhaled air to vent away from the patient's face.

According to another aspect of the disclosure, at least one air vent is disposed in communication with the exhalation valve.

According to another aspect of the disclosure, the at least one air vent is located on an exterior sidewall of the chamber housing.

According to another aspect of the disclosure, the mouthpiece further comprises a shroud portion configured to cover a side of the output end of the chamber housing and at least partially cover the at least one air vent.

According to another aspect of the disclosure, the at least one air vent is located on the mouthpiece.

According to another aspect of the disclosure, plurality of air vents are disposed around a circumference of the mouthpiece.

According to another aspect of the disclosure, a flow indicator is connected to the inhaler adapter and extends into the interior space of the chamber housing, the flow indicator configured to indicate an inhalation flow rate to the user.

According to another aspect of the disclosure, the flow indicator comprises an audible signaling portion and a visual signaling portion.

According to another aspect of the disclosure, the visual signaling portion is located within an inhalation flowpath.

According to another aspect of the disclosure, the visual signaling portion comprises a pinwheel configured to spin in response to an inhalation airflow.

According to another aspect of the disclosure, the audible signaling portion includes a noisemaker configured to make an audible sound if the inhalation flow rate exceeds a predetermined level.

According to another aspect of the disclosure, the noisemaker may be a whistle.

According to another aspect of the disclosure, the inhaler adapter comprises an inhaler port having a flexible cover.

According to another aspect of the disclosure, the flexible cover comprises an elastomeric wing.

According to another aspect of the disclosure, an aerosol inhalation device for use with an inhaler comprises: an aerosol holding chamber including a housing defining a distal end, a proximal end, and an interior space between the distal and proximal ends configured to hold an administered dose of aerosol from the inhaler; a mouthpiece coupled to the distal end of the housing; an adapter coupled to the proximal end of the housing, the adapter configured to removably couple to the inhaler; and a valve member operable to allow a flow of aerosol to pass from the interior space of the chamber housing to the mouthpiece but not to the atmosphere during inhalation, and further operable to allow a flow of exhaled air to pass from the mouthpiece to the atmosphere but not to the interior space of the chamber housing during exhalation.

According to another aspect of the disclosure, a method of administering a dose of aerosol medication to a patient from a metered-dose inhaler comprises: providing an aerosol inhalation spacer comprising: an aerosol holding chamber including a housing defining a distal end, a proximal end, and an interior space between the distal and proximal ends configured to hold an administered dose of aerosol from the inhaler; a mouthpiece coupled to the distal end of the housing; an adapter coupled to the proximal end of the housing, the adapter configured to removably couple to the inhaler; and a valve member operable to allow a flow of aerosol to pass from the interior space of the chamber housing to the mouthpiece but not to the atmosphere during inhalation, and further operable to allow a flow of exhaled air to pass from the mouthpiece to the atmosphere but not to the interior space of the chamber housing during exhalation; mounting the metered-dose inhaler to the holding chamber by inserting a dispensing portion of the inhaler through an aperture in the adapter; dispensing a dose of the aerosol medication from the metered-dose inhaler into the interior space of the holding chamber to mix with air in the chamber for inhalation by a patient through the mouthpiece.

There has thus been outlined certain aspects of the disclosure in order that the detailed description thereof may be better understood, and in order that the present contribution to the art may be better appreciated. There are additional implementations of the disclosure that will be described below and which form the subject matter of the claims appended hereto.

In this respect, before explaining at least one aspect of the aerosol inhalation device in detail, it is to be understood that the aerosol inhalation device is not limited in its application to the details of construction and to the arrangements of the components set forth in the following description or illustrated in the drawings. The aerosol inhalation device is capable of aspects in addition to those described, and of being practiced and carried out in various ways. Also, it is to be understood that the phraseology and terminology employed herein, as well as the abstract, are for the purpose of description and should not be regarded as limiting.

BRIEF DESCRIPTION OF THE DRAWINGS

Implementations of the aerosol inhalation device of the present disclosure are described with reference to the drawings, in which like reference numerals refer to like parts throughout.

DETAILED DESCRIPTION

Figure 1:
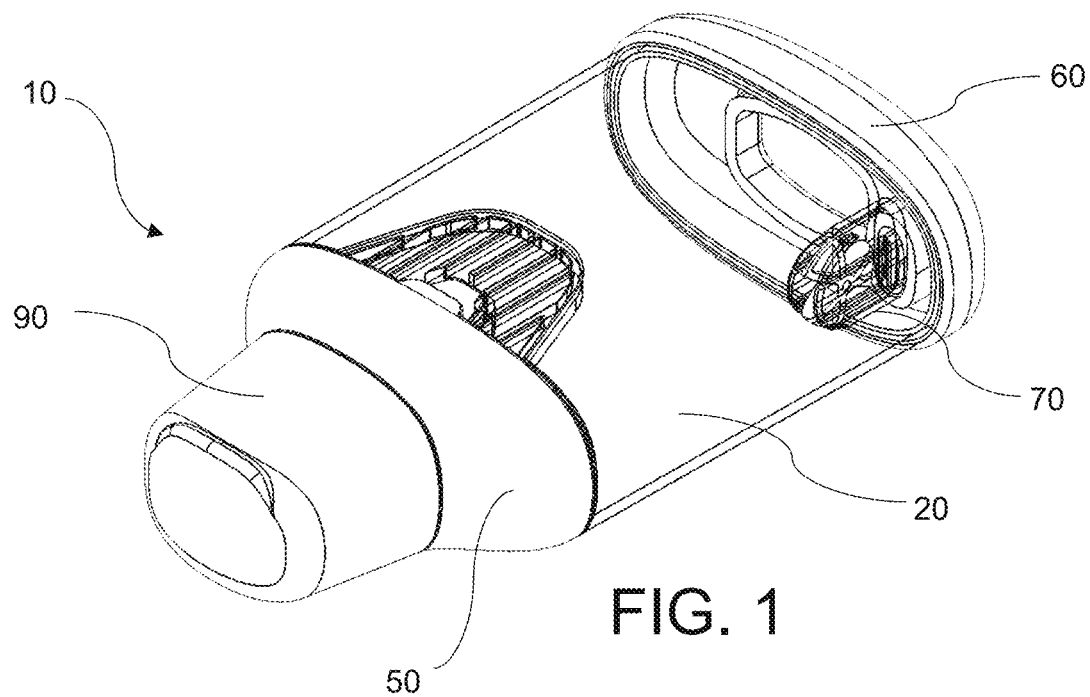
FIG. 1 illustrates a top perspective view of an aerosol inhalation device according to the present disclosure.
Figure 2:
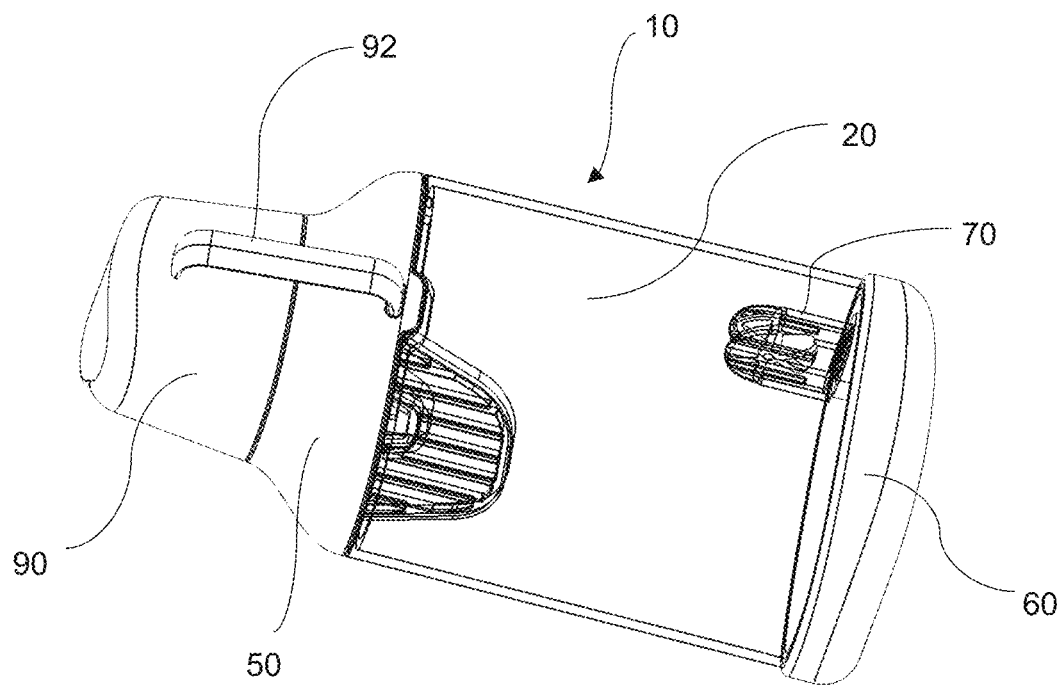
FIG. 2 illustrates a bottom perspective view of the aerosol inhalation device of FIG. 1.
Figure 3:
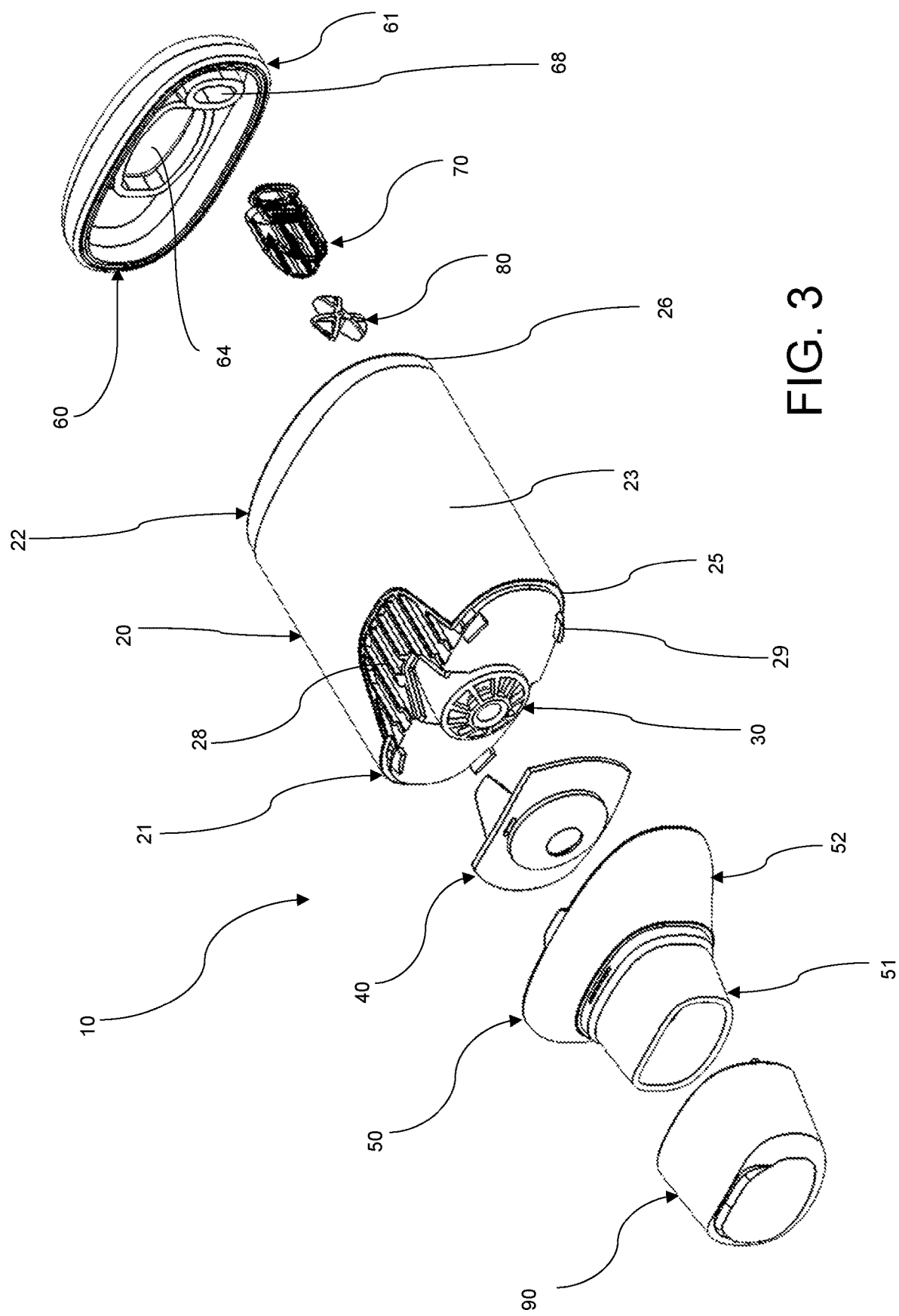
FIG. 3 illustrates an exploded perspective view of the aerosol inhalation device of FIG. 1.
Figure 4:
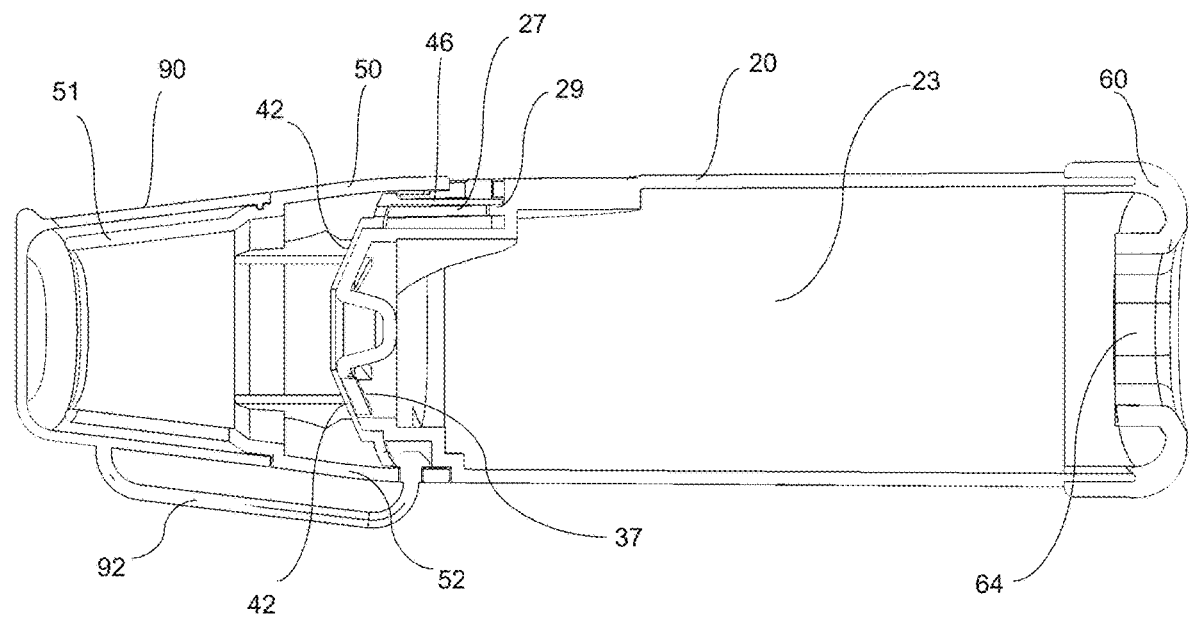
FIG. 4 illustrates a side elevation cross-sectional view of the aerosol inhalation device of FIG. 1.
Figure 5:
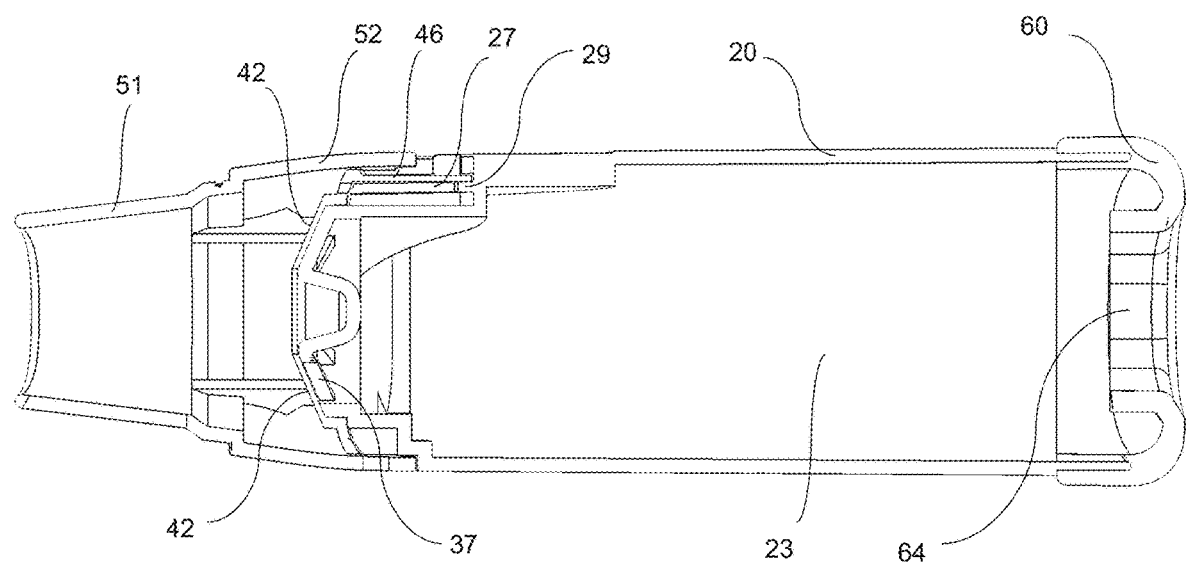
FIG. 5 illustrates a side elevation cross-sectional view of the aerosol inhalation device of FIG. 1 with an endcap removed from a mouthpiece.
Figure 6:
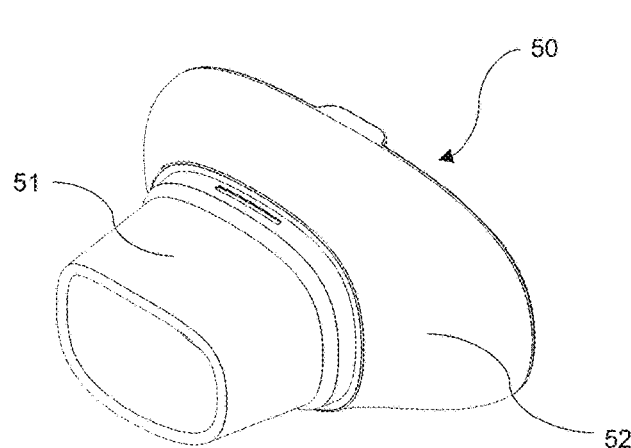
FIG. 6 illustrates a front perspective view of a mouthpiece according to an aspect of the disclosure.

The present disclosure provides an aerosol inhalation device or spacer 10 for use with a metered-dose inhaler (MDI) for the administration of aerosolized medication to a patient. Referring to FIGS. 1-5, the spacer 10 comprises an aerosol holding chamber 20, a flow control member 30, a valve member 40, a mouthpiece 50, an MDI adapter 60, a flow indicator 70, and a removable mouthpiece cap 90. The holding chamber 20 may be transparent so that a user can visibly see a portion of the flow indicator 70 during inhalation, as will be discussed in detail below. The holding chamber 20 comprises an antistatic polymer plastic that reduces static build-up and minimizes static charge for administering consistent medication delivery.

The holding chamber 20 has a slim profile, such as an oval shaped cross-section, for easy storage and placement within a user's pocket. The holding chamber includes a distal end or output end 21 configured to releasably engage the mouthpiece 50, a proximal end or input end 22 configured to releasably engage the MDI adapter 60, and an interior space 23 between the distal and proximal ends. During operation of the spacer, the distal end 21 represents a downstream portion of the chamber, and the proximal end 22 represents an upstream portion of the chamber.

The mouthpiece 50 is located on the outside of the downstream portion of the chamber and the MDI port 60 is located on the outside of the upstream portion. Turning briefly to FIGS. 6-9, the mouthpiece 50 includes a distal portion having an oval-shaped profile for comfortable placement within a user's mouth. The mouthpiece cap 90 may similarly have a corresponding oval-shaped profile for fitting over the distal portion 51 of the mouthpiece 50. It should be appreciated that the distal portion 51 of the mouthpiece 50 may have other shape profiles, including circular, rectangular, and trapezoidal, among others, and the mouthpiece cap 90 may similarly have a corresponding shape profile. A tether 92 has a first end attached to a proximal end 52 of the mouthpiece 50 and second end attached to the mouthpiece cap 90 to ensure that the cap does not get lost once removed from the mouthpiece.

Figure 7:
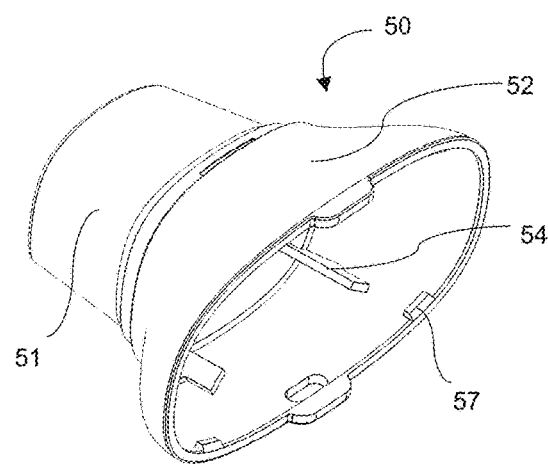
FIG. 7 illustrates a rear perspective view of the mouthpiece of FIG. 6.
Figure 8:
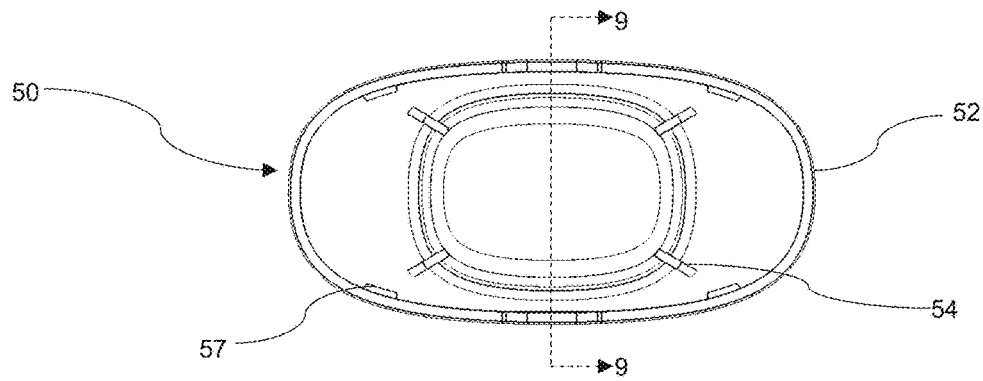
FIG. 8 illustrates a rear elevation view of the mouthpiece of FIG. 6.
Figure 9:
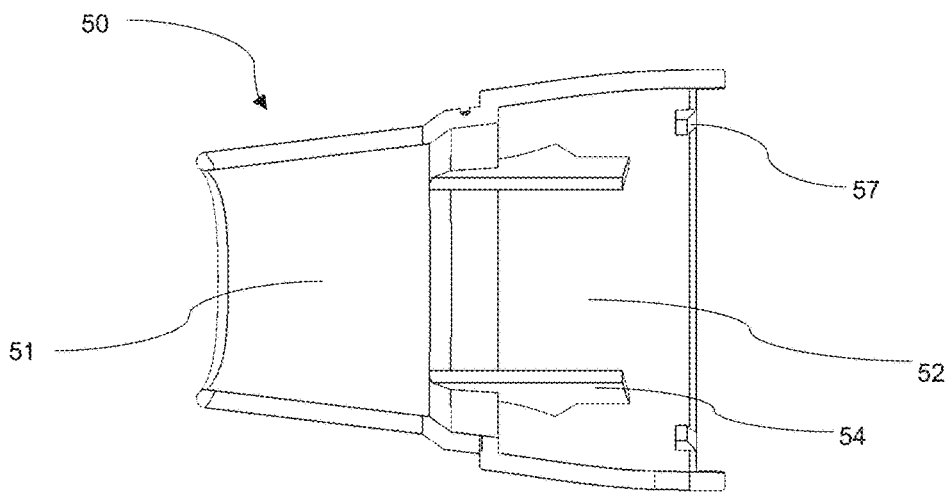
FIG. 9 illustrates a side elevation cross-sectional view of the mouthpiece taken along line 9-9 in FIG. 8.

Referring again to FIGS. 1-5, a distal ledge 25 is formed on the distal end 21 of the holding chamber 20 for sealingly mating with a proximal end 52 of the mouthpiece, and a proximal ledge 26 is formed on the proximal end 22 of the holding chamber for sealingly mating with a distal end 61 of the MDI adapter 60. Locking tabs 29 are also provided spaced apart around the outside of the distal end 21 of the holding chamber for releasably engaging corresponding retention tabs 57 formed on the proximal end 52 of the mouthpiece in a snap-fit manner, as shown in FIGS. 7-9. Accordingly, the spacer components may be readily assembled and dissembled for easy cleaning. In some implementations, the mouthpiece 50 may be secured to the holding chamber using adhesive or other fastening means. The mouthpiece 50 may further include spaced apart retaining ribs 54 for securely holding the valve member 40 in place.

Figure 14:
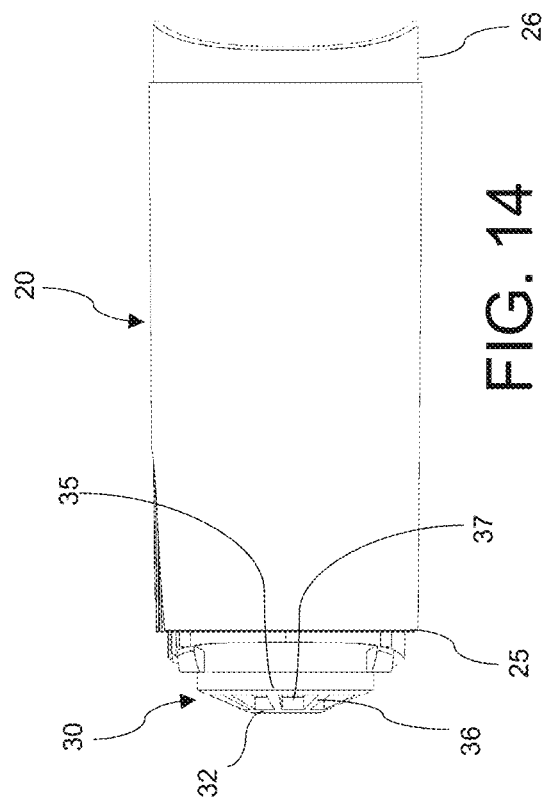
FIG. 14 illustrates a side elevation view of the holding chamber according to an aspect of the disclosure.
Figure 13:
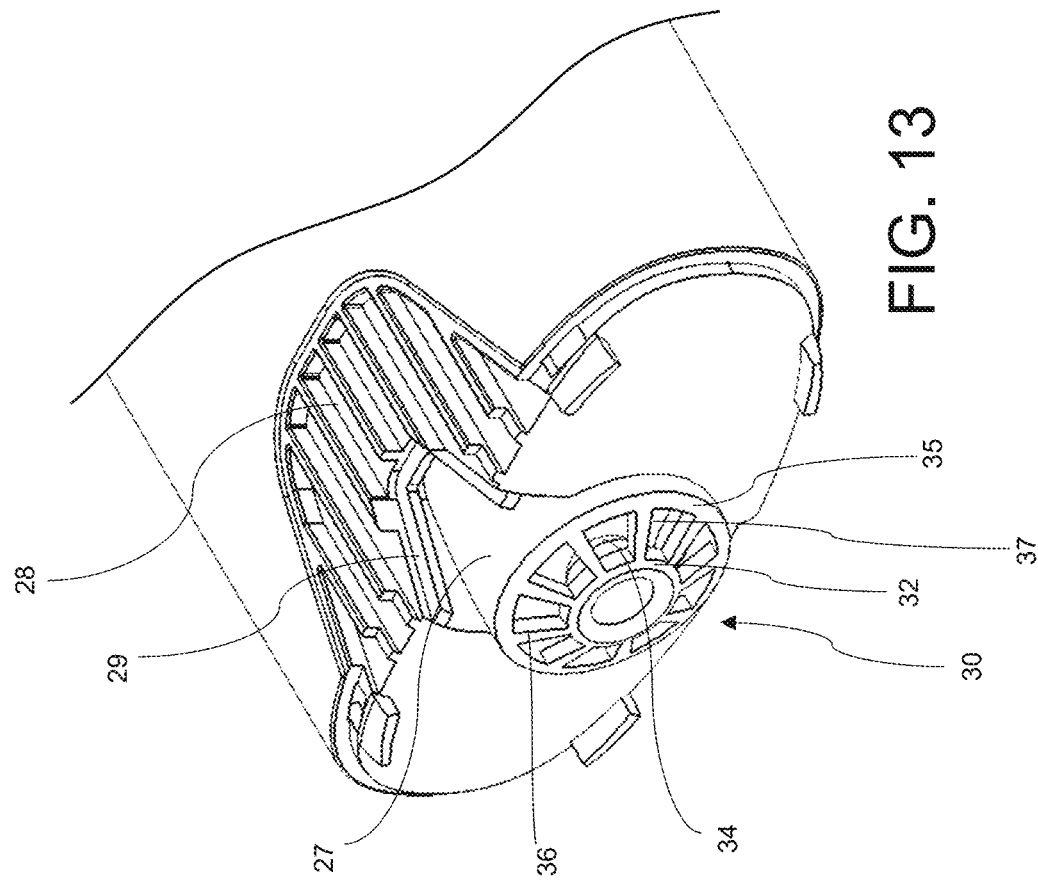
FIG. 13 illustrates a partial perspective view of a holding chamber according to an aspect of the disclosure.

A flow control member 30 is provided on the distal end 21 of the holding chamber 20 and may be integrally formed therewith. In some implementations, the flow control member 30 may be mounted to the distal end 21 of the holding chamber 20. The flow control member 30 is configured to cooperate with the valve member 40 to form a one-way inhalation valve and a one-way exhalation valve. As depicted in FIGS. 13-14, the flow control member 30 includes an annular inspiratory valve seat 32, a flow baffle 34, an annular retaining ledge 35, and connecting members 36. Inhalation openings 37 are disposed between the inspiratory valve seat 32 and the retainer 35. In particular, the inhalation openings 37 are located between adjacent connecting members 36 around the perimeter of the inspiratory valve seat.

Figure 15:
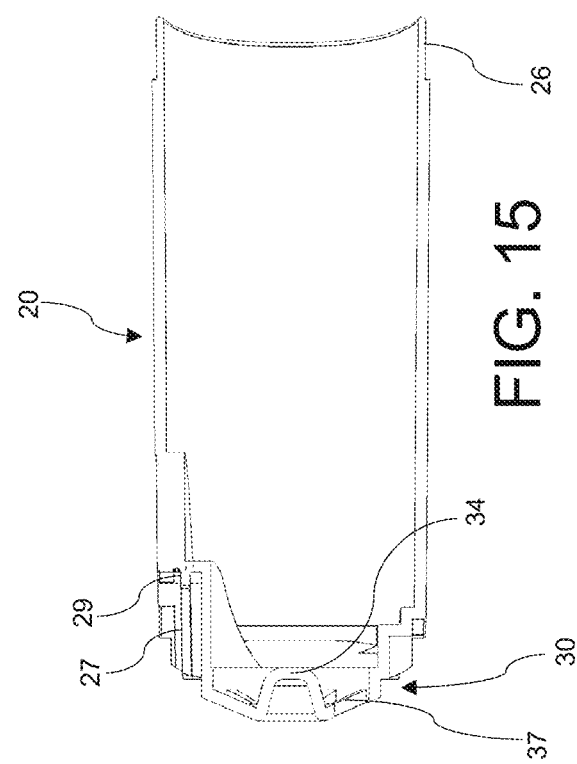
FIG. 15 illustrates a side elevation cross-sectional view of the holding chamber taken along its central longitudinal axis.

The flow baffle 34 is located centrally on the distal end 21 of the chamber 20 and is operatively attached with the retainer 35 by the connecting members 36. The flow baffle 34 is positioned to partially block the outlet end of the holding chamber 20. As shown in FIG. 15, the flow baffle 34 may be dome shaped and has a concave surface and a convex surface. The flow baffle 34 is aligned with a central axis of the holding chamber and is directly in line with a discharge orifice of the MDI. The flow baffle 34 acts as an impact surface for aerosol projected from the MDI and reduces the downstream flow velocity of the aerosol medication particles.

The flow control member 30 further comprises an expiratory valve seat 29 formed in a side wall of the holding chamber and defining an exhalation port 27 in communication with an exhalation or air vent 28 disposed on a side of the holding chamber 20. The vent 28 includes a rectangular shaped recess or channel formed on an outer surface of the chamber 20 and extending from the distal end 21 of the chamber along a portion of the length of the chamber. In some implementations, a plurality of exhalation vents 28 may be provided. The exhalation vents 28 are located in communication with the one-way exhalation valve in order to avoid the entrainment of ambient air into the mouthpiece 50 during a patient's inhalation of the aerosol medication from the interior space 23 of the chamber 20.

Figure 10:
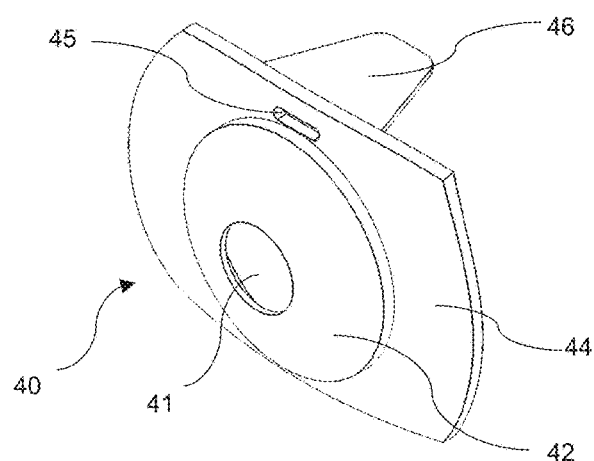
FIG. 10 illustrates a front perspective view of a valve member according to an aspect of the disclosure.
Figure 11:
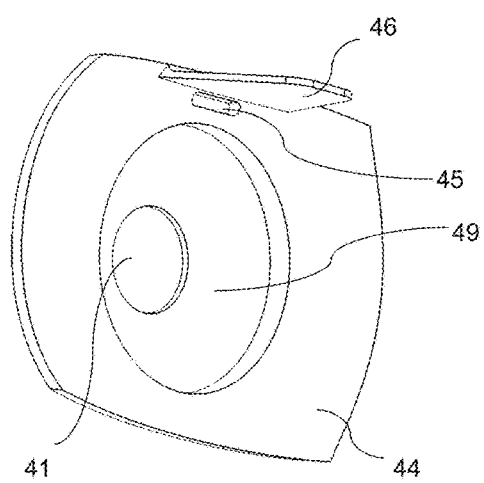
FIG. 11 illustrates a rear perspective view of the valve member of FIG. 10.
Figure 12:
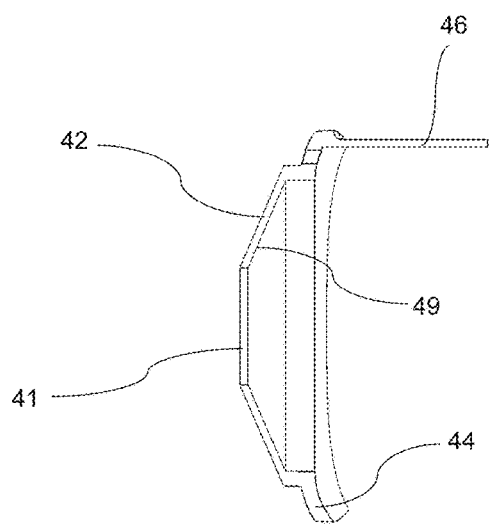
FIG. 12 illustrates a side elevation cross-sectional view of the valve member of FIG. 10.

The valve member 40 is configured to allow aerosol medication to be withdrawn through the mouthpiece 50 but prevents backflow into the chamber housing 20. Referring to FIGS. 10-12, the valve member 40 is adapted to be disposed in the mouthpiece 50 and includes an annular inner portion or flap 42 and an outer portion 44. The outer portion 44 is adapted to sealingly connect to a portion of the distal end of the holding chamber, such as with adhesive or other fastening means. In some implementations, the outer portion 44 may be molded to the distal end of the holding chamber. The annular inner portion 42 defines a central opening 41 and a sealing surface 49. The sealing portion 49 is formed along the inner periphery of the inner portion 42 and forms a continuous surface configured to selectively cover the inhalation openings 37 of the flow control member.

The sealing surface 49 of the valve member 40 is configured to sit on the inspiratory valve seat 32 when the device is not in use, as well as when a user exhales through the mouthpiece, such that the annular inner portion 42 covers and blocks the inhalation openings 37. The central opening 41 of the valve member 40 is circular shaped. In some implementations, the central opening 41 may be square shaped, rectangular shaped, triangular shaped, trapezoidal shaped, or elliptical shaped, among others. The valve member 40 may be made of a flexible material such as silicone, a thermoplastic elastomer, or rubber, among others.

The inspiratory valve seat 32 is formed on the outer perimeter of the concave surface of the flow baffle 34. The sealing surface 49 of the valve member 40 is sized and shaped to sealingly meet with the inspiratory valve seat 32. During operation of the spacer, the user actuates the MDI to cause a plume of aerosol medication to be discharged therefrom and into the interior space 23 of the holding chamber 20. The user then inhales the aerosol medication from the interior space 23 via the mouthpiece 50 of the spacer. The act of inhalation causes the annular inner portion 42 of the valve member 40 to move to an open or first position in which the sealing surface 49 of the valve member is lifted from the inspiratory valve seat 32 of the flow control member 30.

Figure 16:
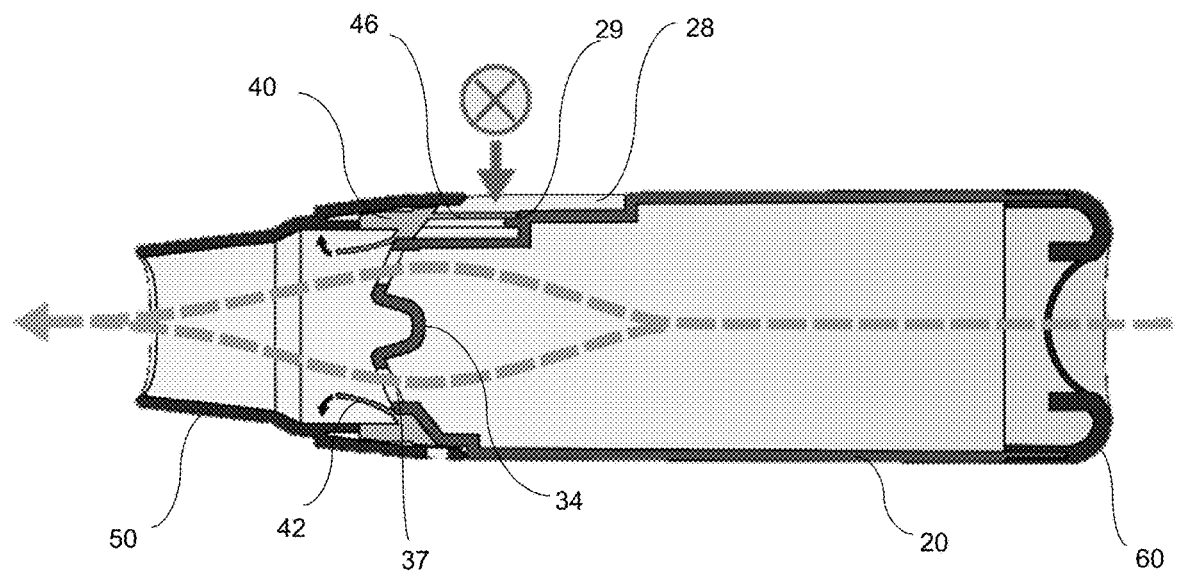
FIG. 16 depicts a cross-sectional view of a spacer according to an aspect of the present disclosure having a valve member in a first position during inhalation in which a one-way inhalation valve is open and a one-way exhalation valve is closed.

Thus, during inhalation, the annular inner portion 42 of the valve member moves in the downstream direction away from the inspiratory valve seat 32 and a gap is created between the sealing surface 49 and the inspiratory valve seat, thus uncovering the inhalation openings 37. In this first position, the outer portion 44 of the valve member is positioned adjacent the retaining ledge 35. Accordingly, the valve member 40 allows aerosol from the interior space 23 to flow through the inhalation openings 37, then through the central opening 41, and then through the mouthpiece 50 to the patient, as illustrated in FIG. 16.

Also in this first position, the valve member 40 blocks the exhalation opening 27. In particular, the valve member 40 further comprises an exhalation flow orifice 45 and a peripheral or auxiliary flap 46 extending from a rear surface thereof. The peripheral flap 46 is configured to sealingly sit on the expiratory valve seat 29 and cover the exhalation opening 27 when the spacer is not in use, as well as when a user inhales through the mouthpiece. Thus, during inhalation the peripheral flap 46 covers and blocks the exhalation port 27 to prevent ambient air from being entrained into the aerosol flow within the mouthpiece. The act of exhalation causes the peripheral flap 46 of the valve member 40 to move to an open or second position.

Figure 17:
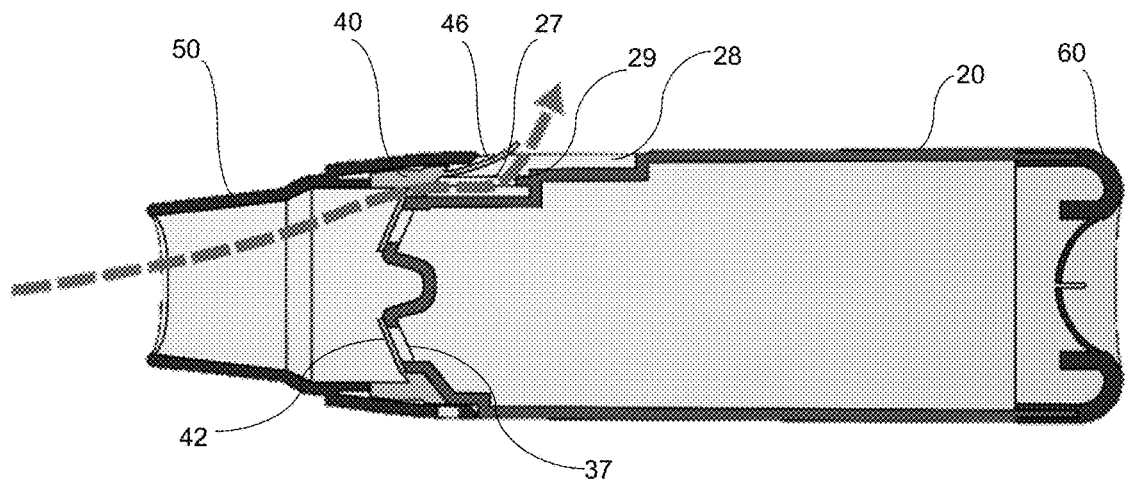
FIG. 17 depicts the cross-sectional view of the spacer of FIG. 16 having the valve member in a second position during exhalation in which the one-way inhalation valve is closed and the one-way exhalation valve is open.

In this second position, as illustrated in FIG. 17, the peripheral flap 46 is lifted from the expiratory valve seat 29 so that exhaled air from the user passes through the mouthpiece 50, then through the exhalation flow orifice 45, and finally out of the exhalation opening 27 to the atmosphere. Furthermore, in this second position, the annular inner portion 42 of the valve member 40 is positioned so that it completely covers the inhalation openings 37, and the sealing surface 49 mates with the inspiratory valve seat 32. In this second position, the valve member 40 prevents exhaled air and aerosol from flowing back into the holding chamber 20 and instead directs this exhaled air and aerosol to flow through the exhalation port 27 into the atmosphere. Exhaled air expelled through the exhalation port 27 is directed away from the user's face via the exhalation vents 28. The proximal end 52 of the mouthpiece 50 forms a shroud over the distal end 21 of the holding chamber 20 and covers a portion of the exhalation port 27 and the peripheral flap 46. The placement of the shroud covering a portion of the exhalation vents help prevent accidental blockage of the exhalation valve during use. Several breaths may be taken if necessary, wherein the operation of the valve member 40 repeats the above described steps.

Figure 18:
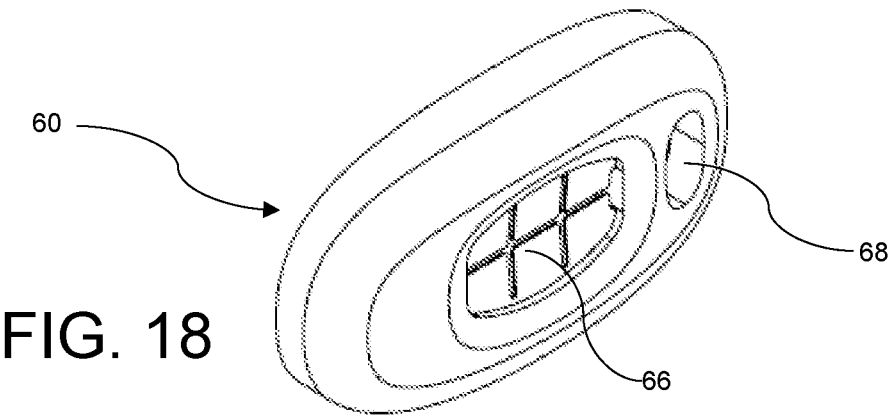
FIG. 18 illustrates a front perspective view of an inhaler adapter according to an aspect of the disclosure.
Figure 19:
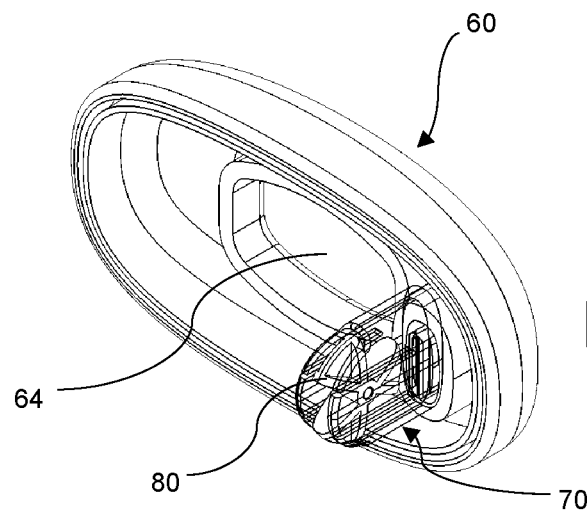
FIG. 19 illustrates a rear perspective view of an inhaler adapter without flexible wings.
Figure 20:
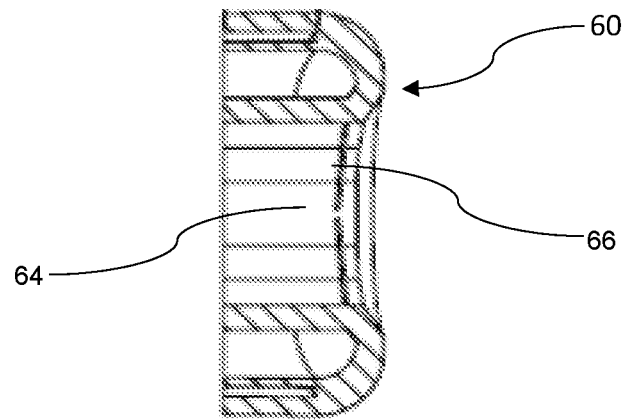
FIG. 20 illustrates a side elevation cross-sectional view of the inhaler adapter of FIG. 18.

Turning to FIGS. 18-20, the MDI adapter 60 may comprise a flexible elastomeric material and is configured to fit over the proximal ledge 26 formed on the proximal end 22 of the holding chamber 20. The adapter 60 comprises an aperture 64 through which a standard MDI mouthpiece may be inserted so as to dispense airborne medication into the interior space 23 of the chamber 20. The aperture may be covered by thin flexible elastomeric wings 66 extending from the periphery of the aperture 64 and forming cross-slits that open to allow a discharge portion of the inhaler to be inserted therethrough. The wings 66 may be integrally molded with the adapter 60 and may be disposed within the aperture 64 in order to close the aperture 64 when no inhaler is inserted therein. The flexible wings 66 prevent dirt, debris, or other foreign material from entering the interior space 23 of the chamber 20 when not in use and/or when an inhaler is not inserted into the MDI aperture. Inserting an MDI mouthpiece into the aperture 64 forces the flexible wings 66 to bend, thus opening the aperture to receive the mouthpiece. The flexible wings 66 also ensure a sealing engagement with the MDI mouthpiece.

The MDI adapter also comprises an ambient air port 68 which opens the interior 23 of the holding chamber 20 to atmosphere so that the user is able to inhale the aerosolized medication dispensed within the chamber once the MDI is activated. The ambient air port 68 may be provided adjacent to the aperture 64 on either side of the adapter 60. The ambient air port 68 is configured to prevent the aerosolized medicine from exiting the interior space of the holding chamber and entering the atmosphere by maintaining a pressure differential therebetween. A flow indicator or breathing indicator 70 is attached to the ambient air port 68.

Figure 21:
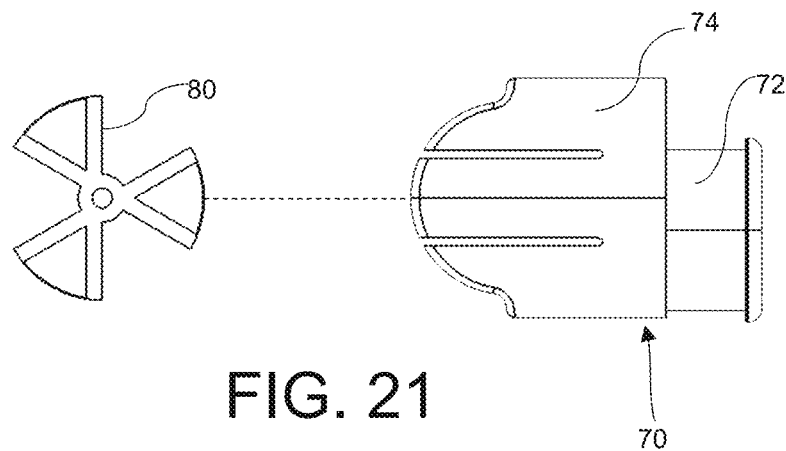
FIG. 21 illustrates a partially exploded side elevation view of a flow indicator in accordance with an aspect of the present disclosure.
Figure 22:
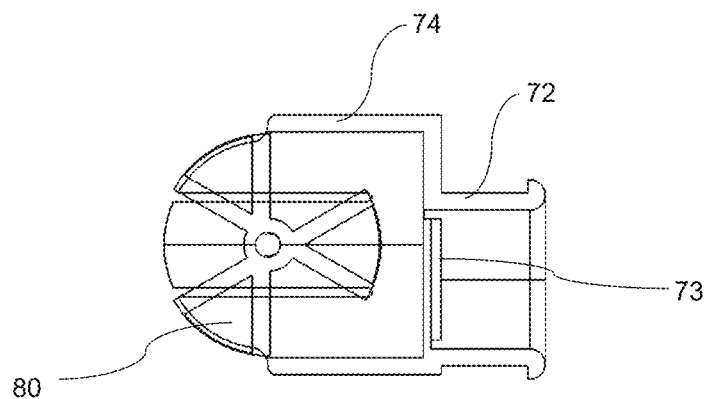
FIG. 22 illustrates a side elevation cross-sectional view of the flow indicator.
Figure 23:
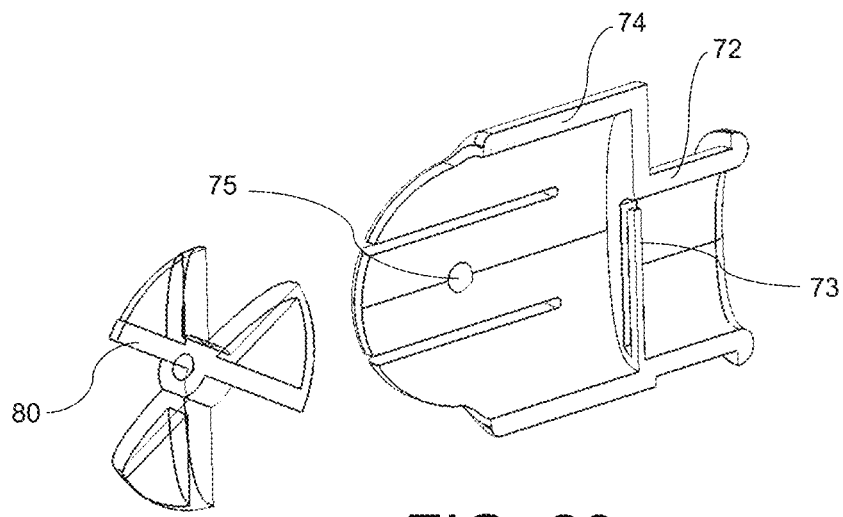
FIG. 23 illustrates an exploded cross-sectional perspective view of the flow indicator.

Referring to FIGS. 21-23, the flow indicator 70 comprises an audible signaling portion 72 and a visual signaling portion 74. The audible signaling portion 72 is mounted in the ambient air port 68 and the visual signaling portion 74 extends longitudinally into the interior space 23 of the holding chamber 20. An ambient air passageway extends through both the audible and visual signaling portions. A noisemaker 73, such as a reed, is provided within the passageway of the audible signaling portion 72. The reed is configured to vibrate when air passes too fast from the inlet end of the flow indicator and through to the outlet end, such as during inhalation. When the reed vibrates it generates a whistle sound that can be readily heard by the user indicating that the inhalation flow rate of aerosolized medicine is too fast and that the user's inhalation should be slowed down.

The visual signaling portion 74 helps the user time their inhalation relative to the MDI actuation, and also assists with breath counting. The visual signaling portion may also let the user know whether inhalation should be slowed down. Specifically, a pinwheel 80 or other spinning device, such as a wind spinner, is attached within the passageway of the visual signaling portion 74 about a swivel joint 75. The pinwheel 80 is configured to spin during inhalation as ambient air is drawn into the interior space of the holding chamber through the passageway of the flow indicator 70. The user is able to visibly see how fast the pinwheel 80 spins during inhalation due to the transparency of the holding chamber 20. Accordingly, when the user sees the pinwheel 80 spinning too fast, the user can slow down their breathing as desired. A proper inhalation flow rate of the aerosolized medicine is important because if the user inhales the aerosol too fast it may not be fully effective. During an asthma attack, for instance, if a user inhales the aerosol medicine too fast it may be drawn past the bronchi and into the lungs where it may not have an optimal effect on the user.

Figure 24:
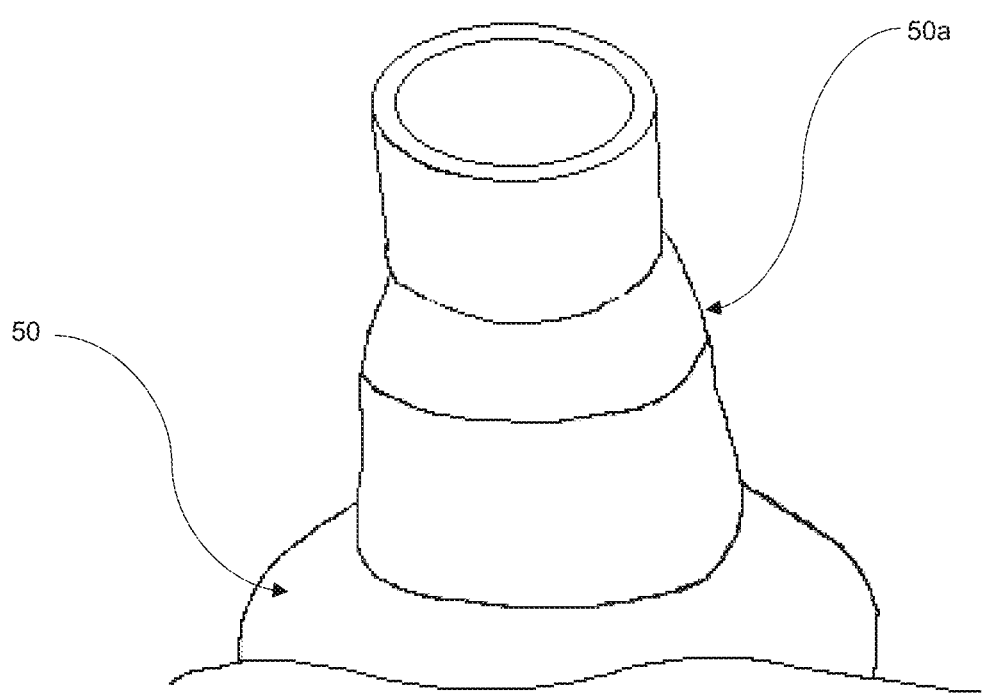
FIG. 24 illustrates a perspective view of a breathing mask adapter in accordance with an aspect of the present disclosure.
Figure 25:
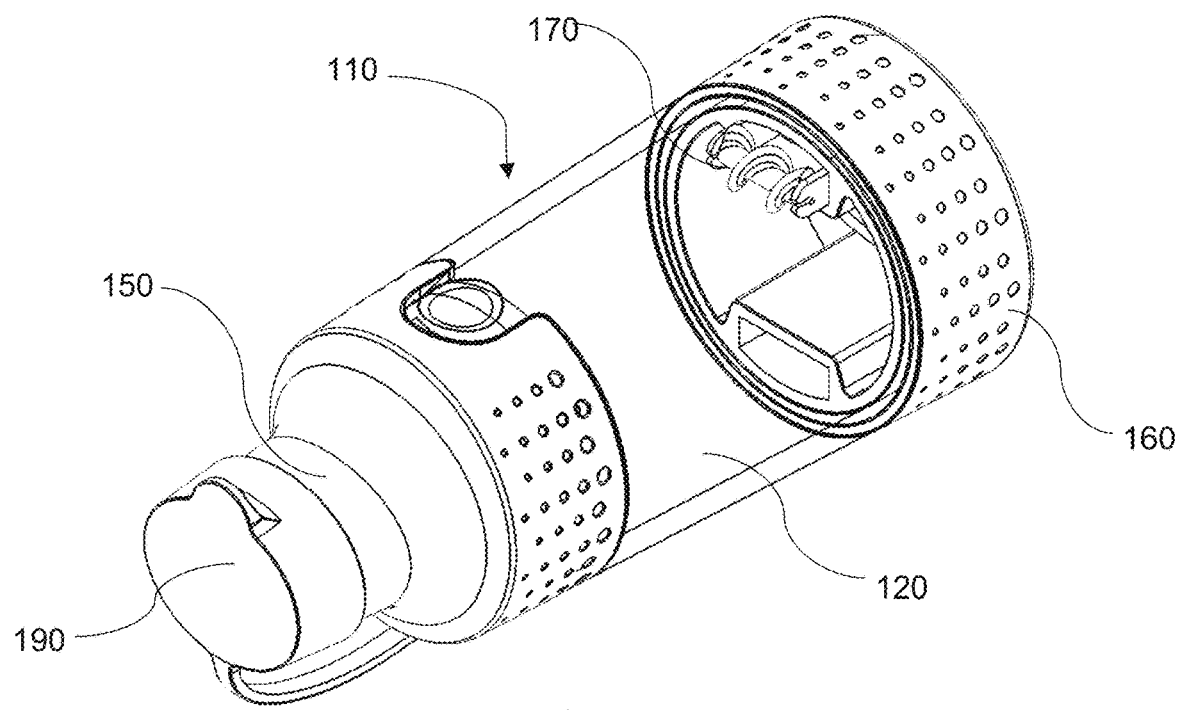
FIG. 25 illustrates a top perspective view of an aerosol inhalation device according to another aspect of the present disclosure.
Figure 26:
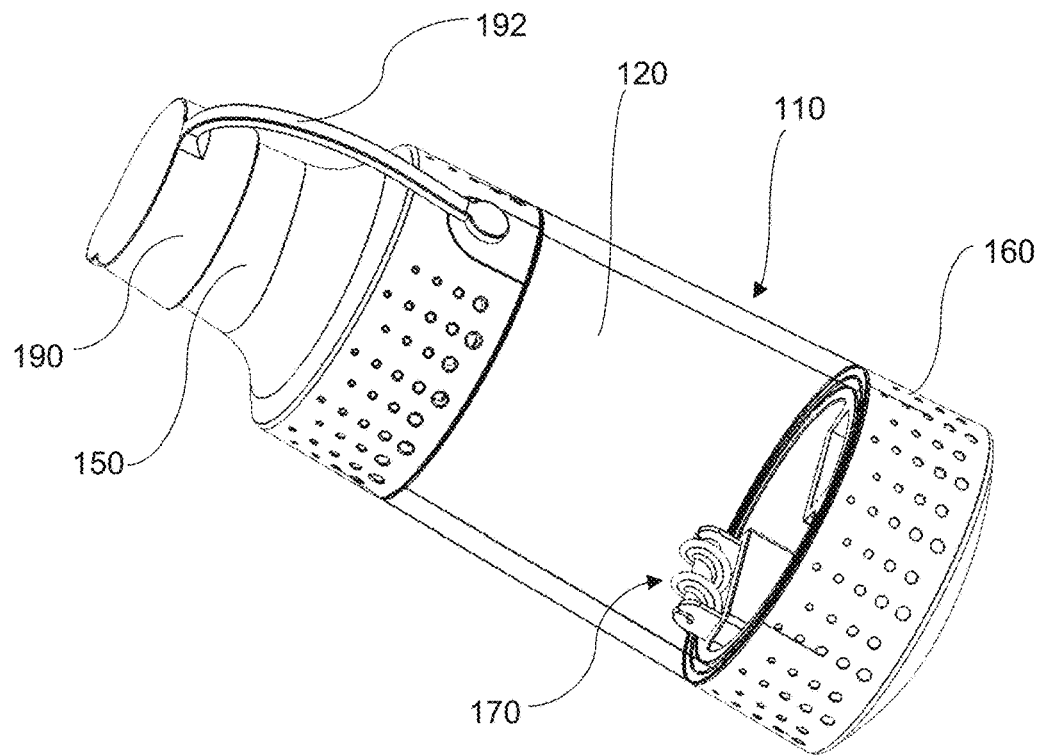
FIG. 26 illustrates a bottom perspective view of the aerosol inhalation device of FIG. 25.
Figure 27:
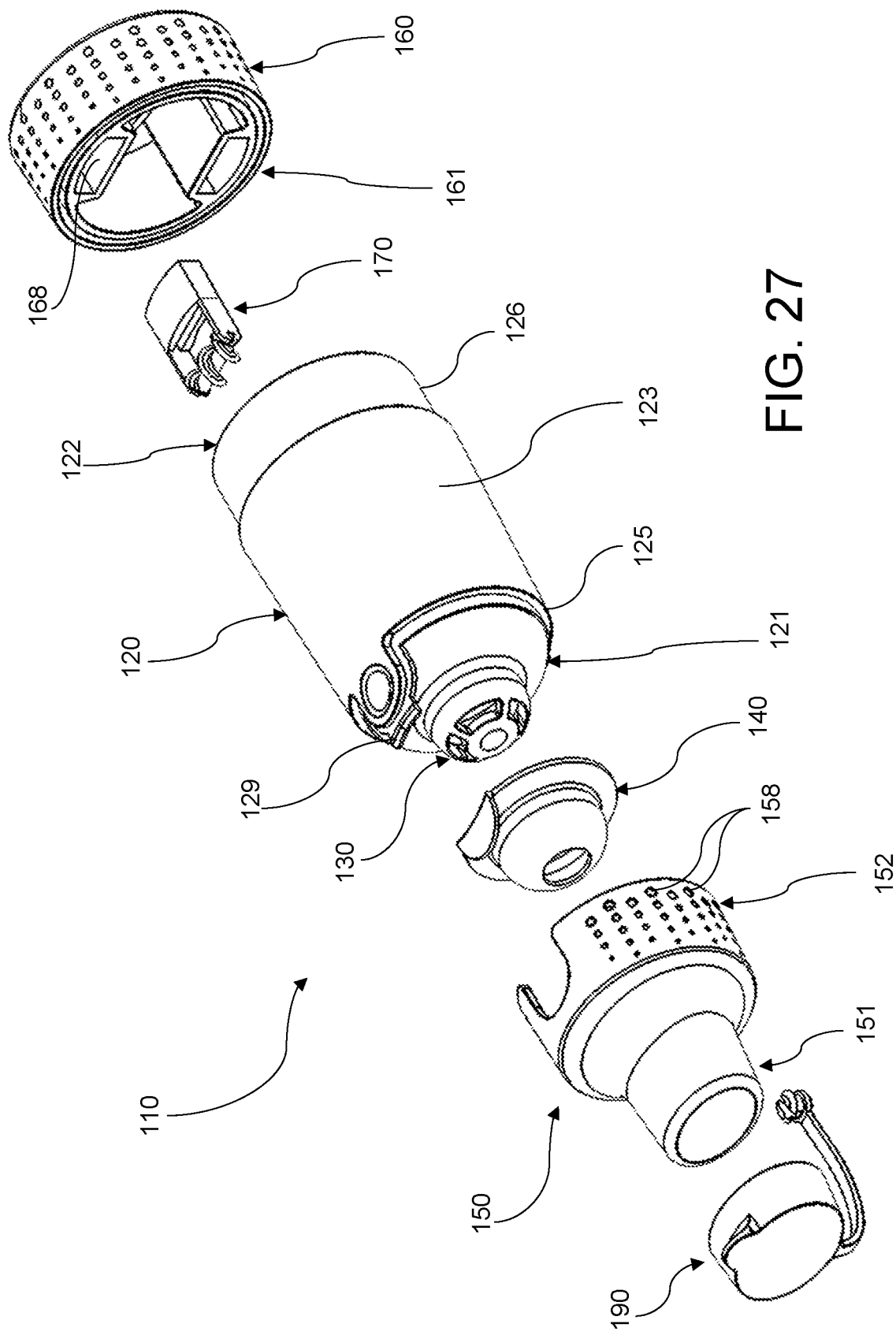
FIG. 27 illustrates an exploded perspective view of the aerosol inhalation device of FIG. 25.

In some implementations, a breathing mask may be releasably attached to the mouthpiece 50 via an adapter 50a. As depicted in FIG. 24, for instance, the adapter 50a includes a portion that is snap-fit over the opening at the distal end 51 of the mouthpiece 50 to offer a 22 mm ISO connection for the breathing mask.

Another implementation of an aerosol inhalation device or spacer 100 for use with a metered-dose inhaler (MDI) for the administration of aerosolized medication to a patient is depicted in FIGS. 25-29. The spacer 110 comprises an aerosol holding chamber 120, a flow control member 130, a valve member 140, a mouthpiece 150, an MDI adapter 160, a flow indicator 170, and a removable mouthpiece cap 90. The holding chamber 120 may be transparent so that a user can visibly see a portion of the flow indicator 170 during inhalation. The holding chamber 120 comprises an antistatic polymer plastic that reduces static build-up and minimizes static charge for administering consistent medication delivery.

The holding chamber 120 has a generally cylindrical or tubular profile. The holding chamber includes a distal end or output end 121 configured to releasably engage the mouthpiece 150, a proximal end or input end 122 configured to releasably engage the MDI adapter 160, and an interior space 123 between the distal and proximal ends. During operation of the spacer, the distal end 121 represents a downstream portion of the chamber, and the proximal end 122 represents an upstream portion of the chamber. In some implementations the holding chamber may have a circular cross-section and be tapered from the proximal end toward the distal end.

The mouthpiece 150 is located on the outside of the downstream portion of the chamber and the MDI port 160 is located on the outside of the upstream portion. Turning briefly to FIGS. 30-33, the mouthpiece 150 includes a distal portion having an oval-shaped profile for comfortable placement within a user's mouth. The mouthpiece cap 190 may similarly have a corresponding oval-shaped profile for fitting over the distal portion 151 of the mouthpiece 150. It should be appreciated that the distal portion 151 of the mouthpiece 150 may have other shape profiles, including circular, rectangular, and trapezoidal, among others, and the mouthpiece cap 190 may similarly have a corresponding shape profile. A tether 192 has a first end attached to a proximal end 152 of the mouthpiece 150 and second end attached to the mouthpiece cap 190 to ensure that the cap does not get lost once removed from the mouthpiece.

Figure 28:
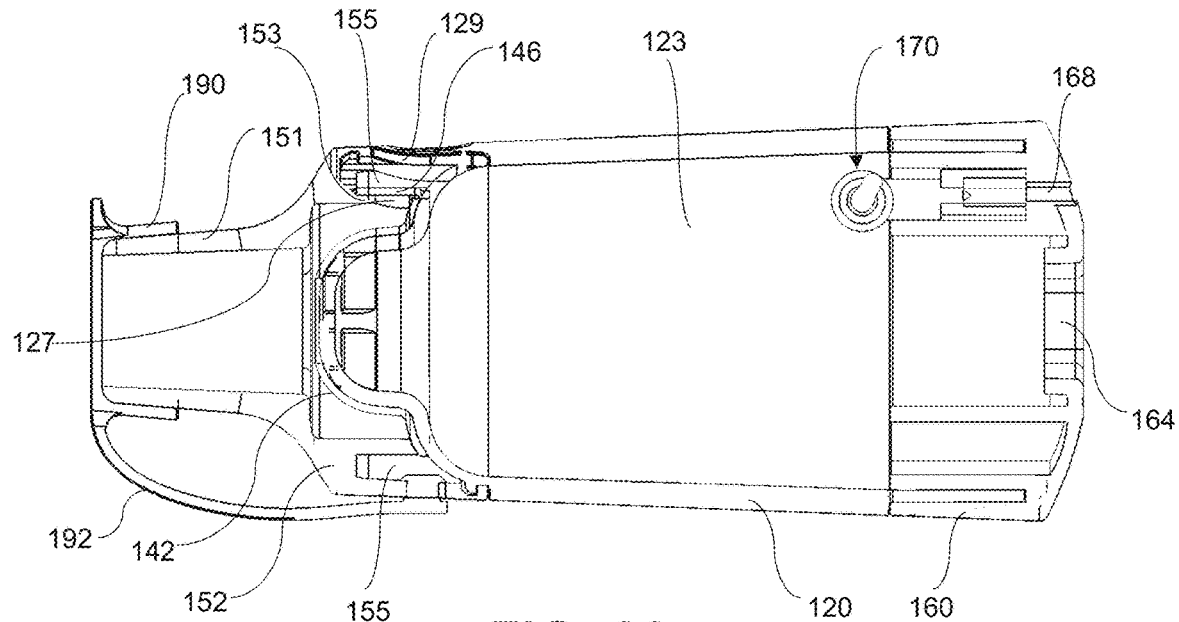
FIG. 28 illustrates a side elevation cross-sectional view of the aerosol inhalation device of FIG. 25.
Figure 29:
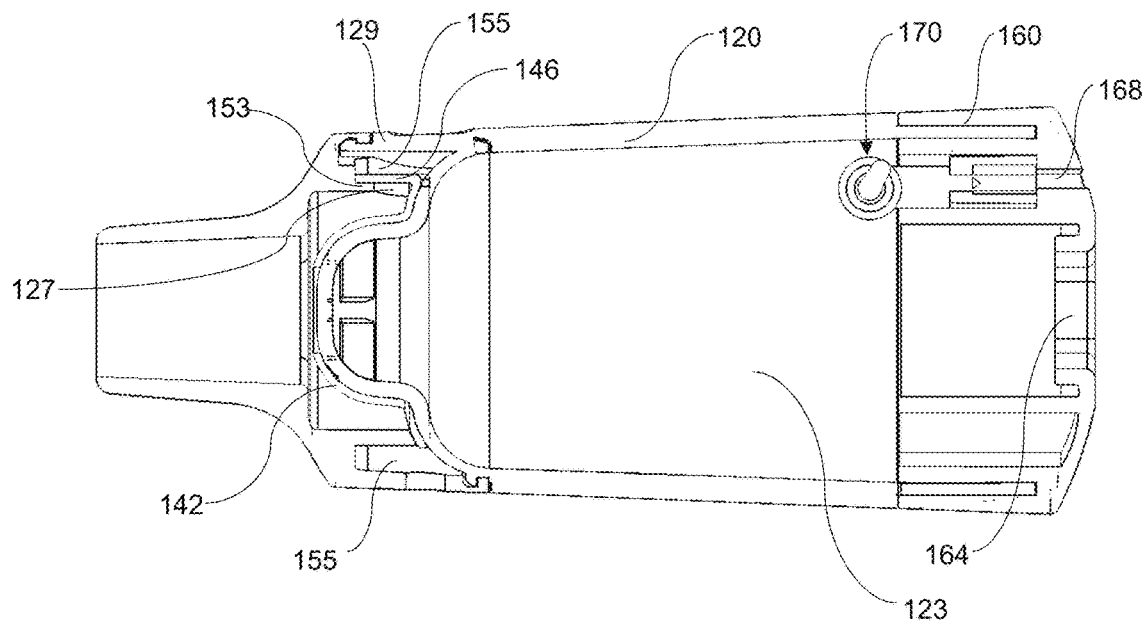
FIG. 29 illustrates a side elevation cross-sectional view of the aerosol inhalation device of FIG. 25 with an endcap removed from a mouthpiece.
Figure 30:
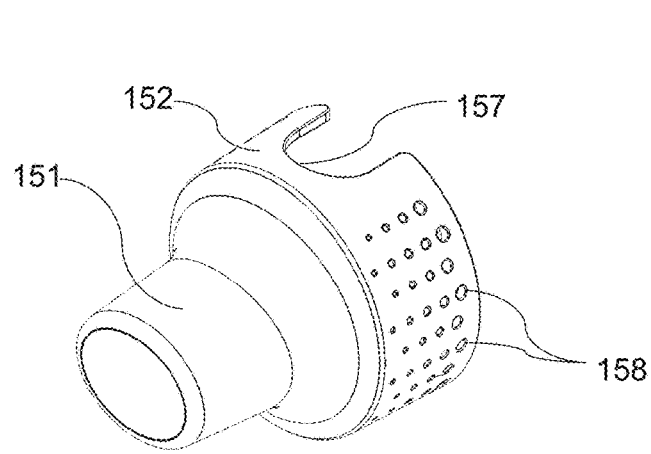
FIG. 30 illustrates a front perspective view of a mouthpiece according to an aspect of the disclosure.
Figure 31:
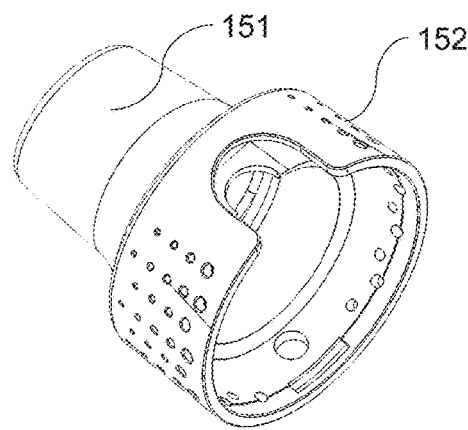
FIG. 31 illustrates a rear perspective view of the mouthpiece of FIG. 30.
Figure 32:
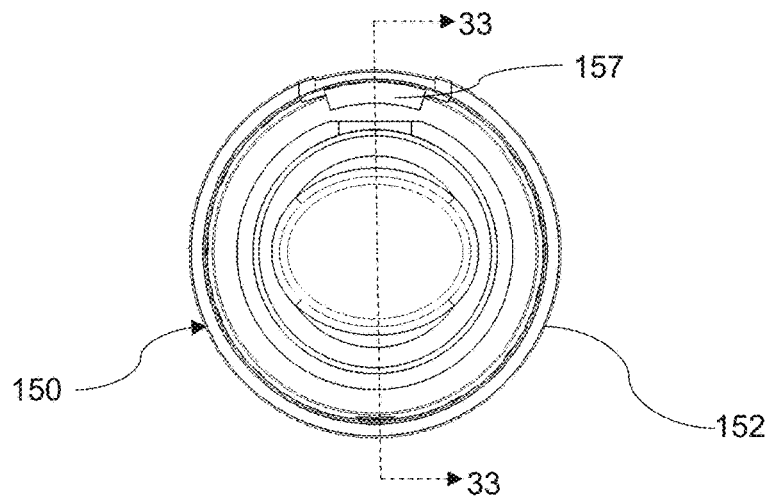
FIG. 32 illustrates a rear elevation view of the mouthpiece of FIG. 30.
Figure 33:
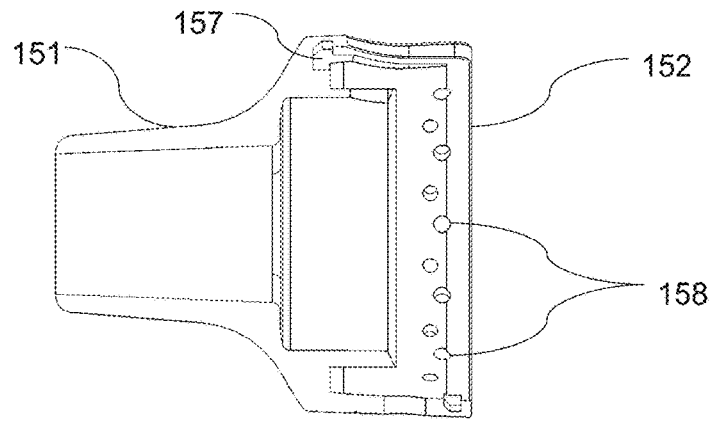
FIG. 33 illustrates a side elevation cross-sectional view of the mouthpiece taken along line 33-33 in FIG. 32.
Figure 34:
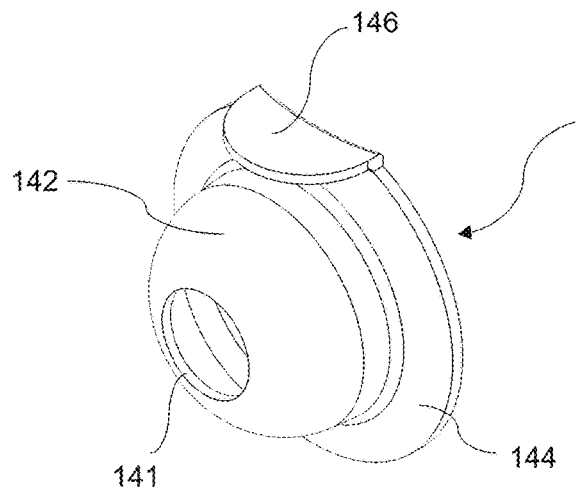
FIG. 34 illustrates a front perspective view of a valve member according to an aspect of the disclosure.
Figure 35:
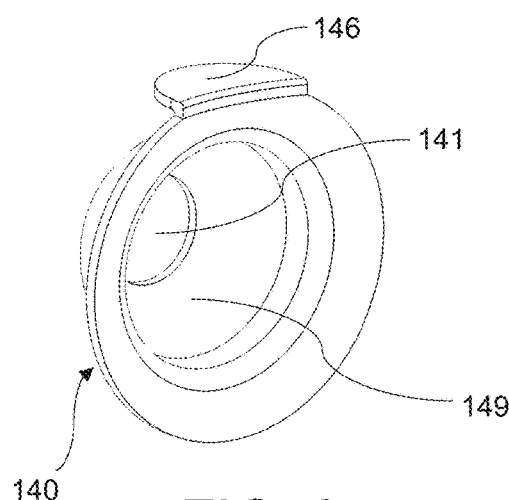
FIG. 35 illustrates a rear perspective view of the valve member of FIG. 34.
Figure 36:
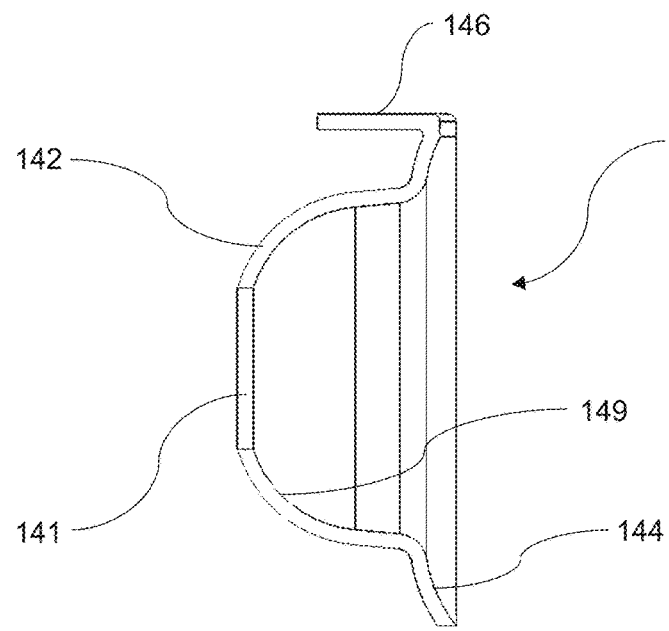
FIG. 36 illustrates a side elevation cross-sectional view of the valve member of FIG. 34.

A distal ledge 125 is formed on the distal end 121 of the holding chamber 120 for sealingly mating with a proximal end 152 of the mouthpiece, and a proximal ledge 126 is formed on the proximal end 122 of the holding chamber for sealingly mating with a distal end 161 of the MDI adapter 160. A locking tab 129 extends from the distal end 121 of the holding chamber for releasably engaging a corresponding retention tab 157 formed on the proximal end 152 of the mouthpiece in a snap-fit manner, as shown in FIGS. 28-29. A user is able to disengage the locking tab 129 from the retention tab 157 by pressing on a push member attached to the locking tab.

Figure 38:
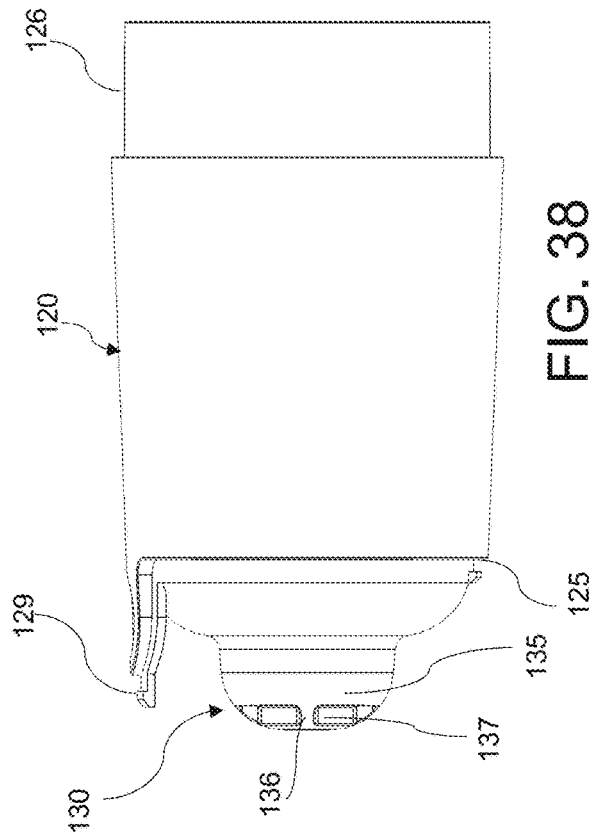
FIG. 38 illustrates a side elevation view of the holding chamber according to an aspect of the disclosure.
Figure 39:
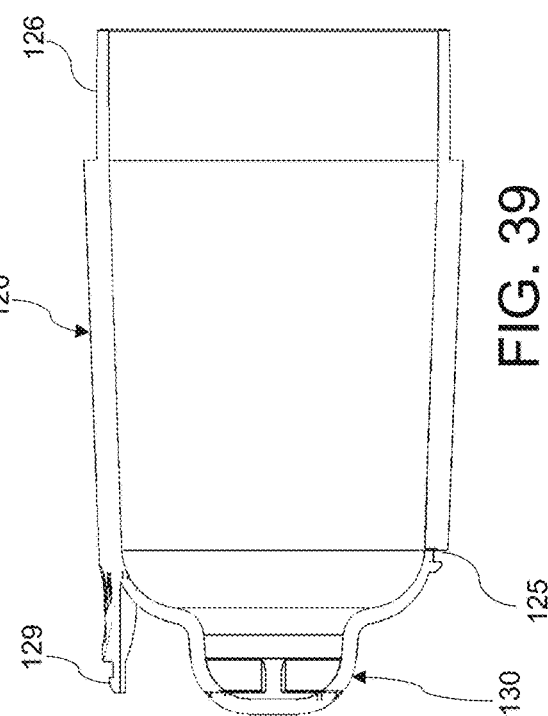
FIG. 39 illustrates a side elevation cross-sectional view of the holding chamber taken along its central longitudinal axis.
Figure 37:
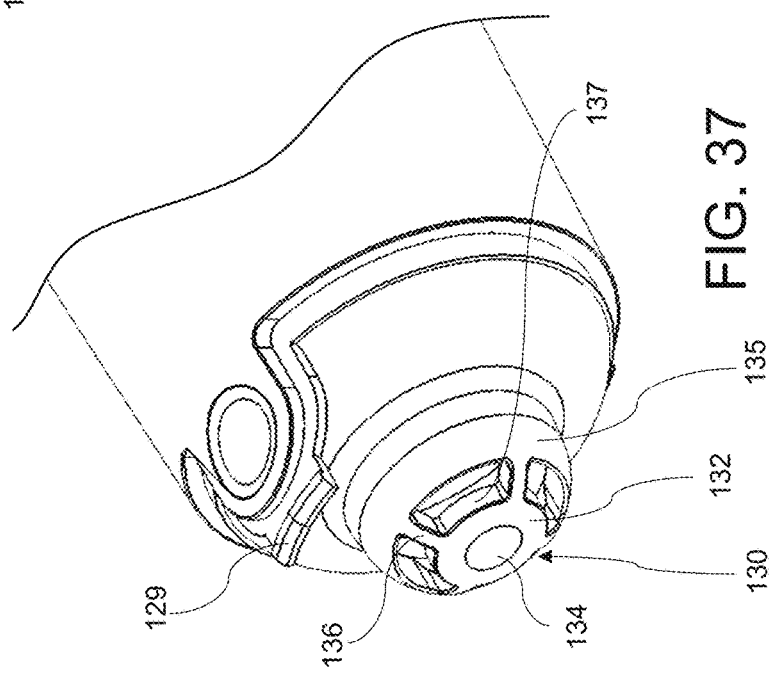
FIG. 37 illustrates a partial perspective view of a holding chamber according to an aspect of the disclosure.

A flow control member 130 is provided on the distal end 121 of the holding chamber 120 and may be integrally formed therewith. In some implementations, the flow control member 130 may be mounted to the distal end 121 of the holding chamber 120. The flow control member 130 is configured to cooperate with the valve member 140 to form a one-way inhalation valve and a one-way exhalation valve. As depicted in FIGS. 37-39, the flow control member 130 includes an annular inspiratory valve seat 132, a flow baffle 134, an annular retaining ledge 135, and connecting members 136. Inhalation openings 137 are disposed between the inspiratory valve seat 132 and the retainer 135. In particular, the inhalation openings 137 are located between adjacent connecting members 136 around the perimeter of the inspiratory valve seat.

The flow baffle 134 is located centrally on the distal end 121 of the chamber 120 and is operatively attached with the retainer 135 by the connecting members 136. The flow baffle 134 is positioned to partially block the outlet end of the holding chamber 120. As shown in FIG. 39, the flow baffle 134 may be flat with a central axis aligned with a central axis of the holding chamber such that it is directly in line with a discharge orifice of the MDI. The flow baffle 134 may act as an impact surface for aerosol projected from the MDI to reduce the downstream flow velocity of the aerosol medication particles.

As will be discussed in further detail below, a portion of the valve member 140 is configured to sit on an expiratory valve seat 153 located within the proximal end 152 of the mouthpiece 150 to form an exhalation valve having an exhalation port 127. The exhalation port 127 is in communication with an exhalation channel 155 annularly disposed within the proximal end of the mouthpiece. An exhalation or air vent 158 is disposed on a side of the mouthpiece 150 and is in fluid communication with the exhalation channel 155. The exhalation vent 158 may be a hole formed on the proximal end of the mouthpiece 150. In some implementations, a plurality of exhalation vents 158 in communication with the annular exhalation channel 155 may be located annularly around a circumference of the proximal end of the mouthpiece to prevent accidental blockage during use. The exhalation vents 158 are located in fluid communication with the one-way exhalation valve in order to avoid the entrainment of ambient air into the mouthpiece 150 during a patient's inhalation of the aerosol medication from the interior space 123 of the chamber 120.

The valve member 140 is configured to allow aerosol medication to be withdrawn through the mouthpiece 150 but prevents backflow into the chamber housing 120. Referring to FIGS. 34-36, the valve member 140 is adapted to be disposed in the mouthpiece 150 and includes an annular inner portion or flap 142 and an annular outer portion 144. The outer portion 144 is adapted to sealingly connect to a portion of the distal end of the holding chamber, such as with adhesive or other fastening means. In some implementations, the outer portion 144 may be molded to the distal end of the holding chamber. The annular inner portion 142 defines a central opening 141 and a sealing surface 149. The sealing portion 149 is formed along the inner periphery of the inner portion 142 and forms a continuous surface configured to selectively cover the inhalation openings 137 of the flow control member The sealing surface 149 of the valve member 140 is configured to sit on the inspiratory valve seat 132 when the device is not in use, as well as when a user exhales through the mouthpiece, such that the annular inner portion 142 covers and blocks the inhalation openings 137. The central opening 141 of the valve member 140 is circular shaped. In some implementations, the central opening 141 may be square shaped, rectangular shaped, triangular shaped, trapezoidal shaped, or elliptical shaped, among others. The valve member 140 may be made of a flexible material such as silicone, a thermoplastic elastomer, or rubber, among others.

The inspiratory valve seat 132 is formed on the outer perimeter of the flow baffle 134. The sealing surface 149 of the valve member 140 is sized and shaped to sealingly meet with the inspiratory valve seat 132. During operation of the spacer, the user actuates the MDI to cause a plume of aerosol medication to be discharged therefrom and into the interior space 123 of the holding chamber 120. The user then inhales the aerosol medication from the interior space 123 via the mouthpiece 150 of the spacer. The act of inhalation causes the annular inner portion 142 of the valve member 140 to move to an open or first position in which the sealing surface 149 of the valve member is lifted from the inspiratory valve seat 132 of the flow control member 130.

Figure 40:
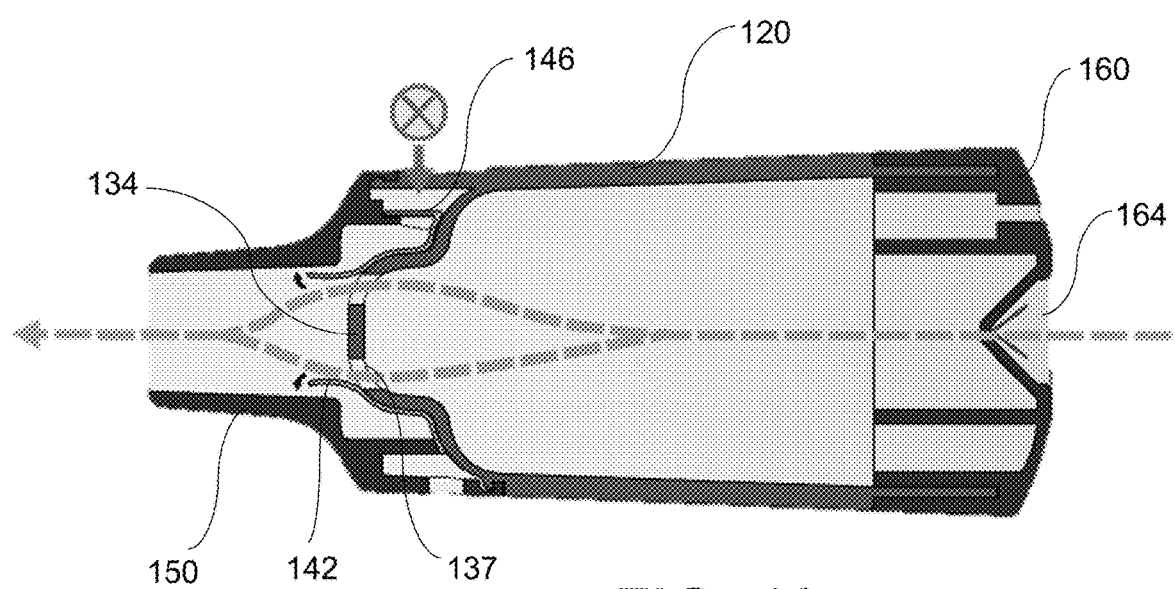
FIG. 40 depicts a cross-sectional view of a spacer according to an aspect of the present disclosure having a valve member in a first position during inhalation in which a one-way inhalation valve is open and a one-way exhalation valve is closed.

Thus, during inhalation, the annular inner portion 142 of the valve member moves in the downstream direction away from the inspiratory valve seat 132 and a gap is created between the sealing surface 149 and the inspiratory valve seat, thus uncovering the inhalation openings 137. In this first position, the outer portion 144 of the valve member is positioned adjacent the retaining ledge 135. Accordingly, the valve member 140 allows aerosol from the interior space 123 to flow through the inhalation openings 137, then through the central opening 141, and then through the mouthpiece 150 to the patient, as illustrated in FIG. 40.

Also in this first position, the valve member 140 blocks the exhalation opening 127. In particular, the valve member 140 further comprises a peripheral or auxiliary flap 146 extending from a front surface thereof. The peripheral flap 146 is configured to sealingly sit on the expiratory valve seat 153 and cover the exhalation opening 127 when the spacer is not in use, as well as when a user inhales through the mouthpiece. Thus, during inhalation the peripheral flap 146 covers and blocks the exhalation port 127 to prevent ambient air from being entrained into the aerosol flow within the mouthpiece. The act of exhalation causes the peripheral flap 146 of the valve member 140 to move to an open or second position.

Figure 41:
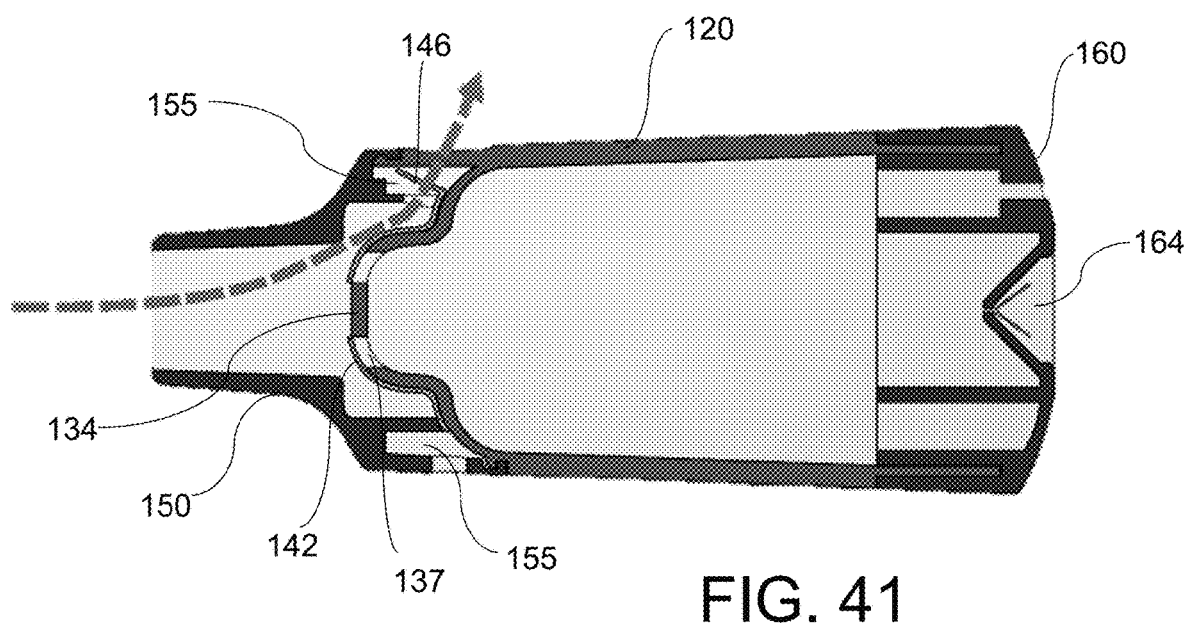
FIG. 41 depicts the cross-sectional view of the spacer of FIG. 40 having the valve member in a second position during exhalation in which the one-way inhalation valve is closed and the one-way exhalation valve is open.

In this second position, as illustrated in FIG. 41, the peripheral flap 146 is lifted from the expiratory valve seat 153 so that exhaled air from the user passes through the mouthpiece 150 and out of the exhalation opening 127. Furthermore, in this second position, the annular inner portion 142 of the valve member 140 is positioned so that it completely covers the inhalation openings 137, and the sealing surface 149 mates with the inspiratory valve seat 132. In this second position, the valve member 140 prevents exhaled air and aerosol from flowing back into the holding chamber 120 and instead directs this exhaled air and aerosol to flow through the exhalation port 127 and into the atmosphere. Thus, the exhalation valve allows the user's exhaled breath to escape into the exhalation channel 155 via passage 127, and finally exit the spacer via exit ports 158. Exhaled air expelled through the exhalation port 127 is directed away from the user's face via the exhalation vents 158.

Figure 42:
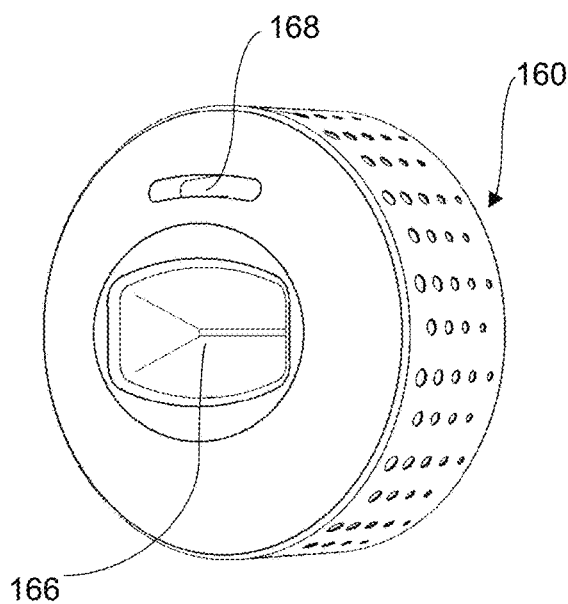
FIG. 42 illustrates a front perspective view of an inhaler adapter according to an aspect of the disclosure.
Figure 43:
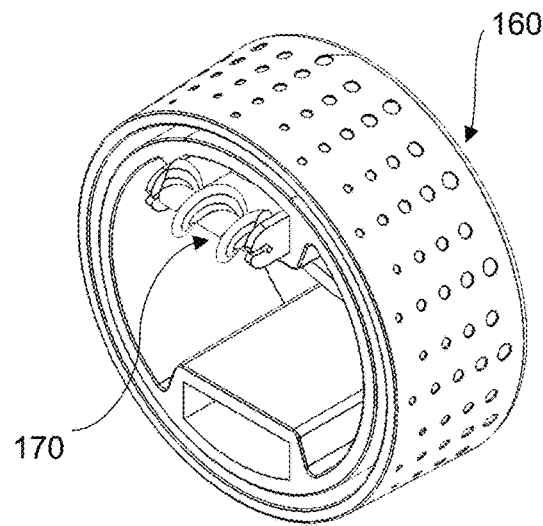
FIG. 43 illustrates a rear perspective view of the inhaler adapter.
Figure 44:
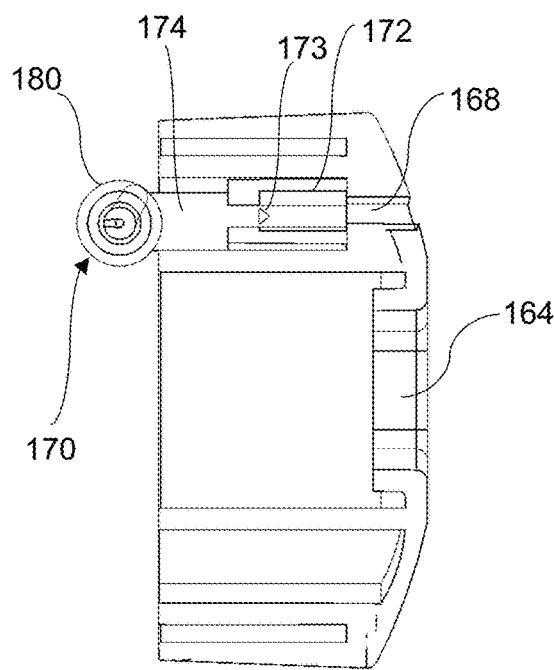
FIG. 44 illustrates a side elevation cross-sectional view of the inhaler adapter.

Turning to FIGS. 42-44, the MDI adapter 160 may comprise a flexible elastomeric material and is configured to fit over the proximal ledge 126 formed on the proximal end 122 of the holding chamber 120. The adapter 160 comprises an aperture 164 through which a standard MDI mouthpiece may be inserted so as to dispense airborne medication into the interior space 123 of the chamber 120. The aperture may be covered by thin flexible elastomeric wings 166 extending from the periphery of the aperture 164 and forming cross-slits that open to allow a discharge portion of the inhaler to be inserted therethrough. The wings 166 may be integrally molded with the adapter 160 and may be disposed within the aperture 164 in order to close the aperture 164 when no inhaler is inserted therein. The flexible wings 166 prevent dirt, debris, or other foreign material from entering the interior space 123 of the chamber 120 when not in use and/or when an inhaler is not inserted into the MDI aperture. Inserting an MDI mouthpiece into the aperture 64 forces the flexible wings 166 to bend, thus opening the aperture to receive the mouthpiece. The flexible wings 166 also ensure a sealing engagement with the MDI mouthpiece.

The MDI adapter also comprises an ambient air port 168 which exposes the interior 123 of the holding chamber 120 to atmosphere so that the user is able to inhale the aerosolized medication dispensed within the chamber once the MDI is activated. The ambient air port 168 may be provided adjacent to the aperture 164 on either side of the adapter 160. The ambient air port 168 is configured to prevent the aerosolized medicine from exiting the interior space of the holding chamber and entering the atmosphere by maintaining a pressure differential therebetween. A flow indicator or breathing indicator 170 is attached to the ambient air port 168.

Figure 45:
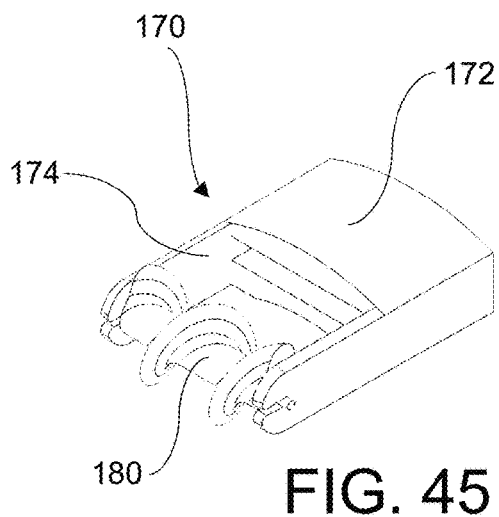
FIG. 45 illustrates a perspective view of a flow indicator.

Referring to FIG. 45, the flow indicator 170 comprises an audible signaling portion 172 and a visual signaling portion 174. The audible signaling portion 172 is mounted in the ambient air port 168 and the visual signaling portion 174 extends longitudinally into the interior space 123 of the holding chamber 120. An ambient air passageway extends through both the audible and visual signaling portions. A noisemaker 173, such as a reed, is provided within the passageway of the audible signaling portion 172. The reed is configured to vibrate when air passes too fast from the inlet end of the flow indicator and through to the outlet end, such as during inhalation. When the reed vibrates it generates a whistle sound that can be readily heard by the user indicating that the inhalation flow rate of aerosolized medicine is too fast and that the user's inhalation should be slowed down.

The visual signaling portion comprises a pinwheel 180 or other spinning device, such as a wind spinner, that is attached to the visual signaling portion 174 about a swivel joint 175. The pinwheel 180 is configured to spin during inhalation as ambient air is drawn into the interior space of the holding chamber through the passageway of the flow indicator 170. The user is able to visibly see how fast the pinwheel 180 spins during inhalation due to the transparency of the holding chamber 120. Accordingly, when the user sees the pinwheel 180 spinning too fast, the user can slow down their breathing as desired. A proper inhalation flow rate of the aerosolized medicine is important because if the user inhales the aerosol too fast it may not be fully effective. During an asthma attack, for instance, if a user inhales the aerosol medicine too fast it may be drawn past the bronchi and into the lungs where it may not have an optimal effect on the user. Thus, the visual signaling portion 174 helps the user time their inhalation relative to the MDI actuation, and also assists with breath counting. The visual signaling portion may also let the user know whether inhalation should be slowed down.

Figure 46:
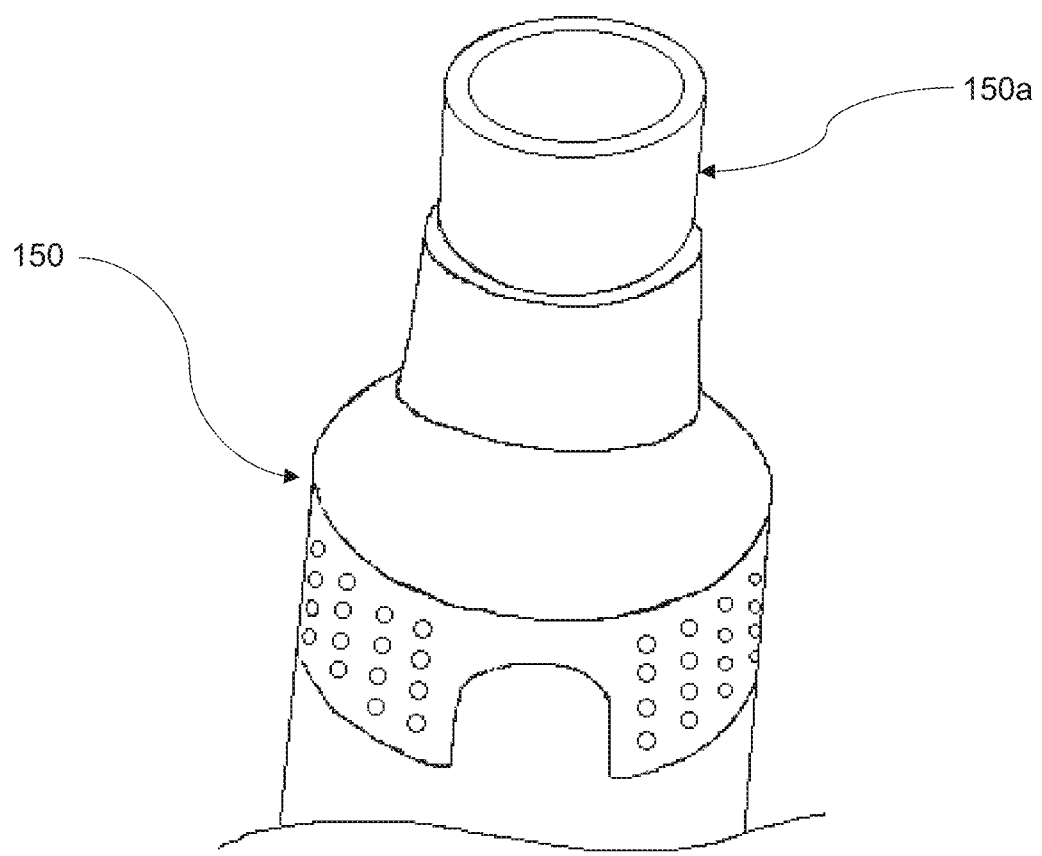
FIG. 46 illustrates a perspective view of a breathing mask adapter in accordance with an aspect of the present disclosure.

In some implementations, a breathing mask may be releasably attached to the mouthpiece 150 via an adapter 150*a*. As depicted in FIG. 46, for instance, the adapter 150*a* includes a portion that is pushed within the opening at the distal end 151 of the mouthpiece and held in place by an interference fit to offer a 22 mm ISO connection for the breathing mask. Additionally, each implementation of the transparent holding chamber described herein may include various types of indicia printed on its exterior surface. The indicia may include instructions for use, or kid-friendly graphics and designs to make the device more appealing to children.

While various features of the present disclosure may be described with respect to MDI devices, the present disclosure is not limited to such MDI devices. The spacer of the present disclosure may be used with a wide variety of inhaler devices.

While the aerosol inhalation device has been described in terms of what may be considered to be specific aspects, the present disclosure is not limited to the disclosed aspects. Moreover, the many features and advantages of the disclosure are apparent from the detailed specification, and thus, it is intended by the appended claims to cover all such features and advantages of the disclosure which fall within the spirit and scope of the disclosure. Further, it is not desired to limit the disclosure to the exact construction and operation illustrated and described, and accordingly, all suitable modifications and equivalents may be resorted to, falling within the scope of the disclosure. Accordingly, the present disclosure should be considered as illustrative and not restrictive. As such, this disclosure is intended to cover various modifications and similar arrangements included within the spirit and scope of the claims, which should be accorded their broadest interpretation so as to encompass all such modifications and similar structures.

What is claimed is:

1. An aerosol inhalation spacer for use with a metered-dose inhaler, the spacer comprising:
   a transparent chamber housing having a body with an input end and an output end and defining an interior space;
   a mouthpiece connected to the output end of the chamber housing;
   an inhaler adapter connected to the input end of the chamber housing; and
   a valve member disposed between the mouthpiece and the output end of the chamber housing, the valve member adapted to cooperate with a portion of the chamber housing to form a one-way inhalation valve and a one-way exhalation valve, the valve member including a concave surface;
   a flow control member disposed on the output end of the chamber housing and having a convex surface that is received within the concave surface of the valve member;
   a flow indicator connected to the inhaler adapter and extending into the interior space of the chamber housing, the flow indicator configured to indicate an inhalation flow rate to the patient, the flow indicator including a rotatable pinwheel that is visible to the patient and is coupled to a whistle, such that an inhalation flowpath is directed to the rotatable pinwheel through the whistle, wherein the flow indicator includes a flow indicator housing, the rotatable pinwheel and the whistle coupled to the flow indicator housing, and wherein the rotatable pinwheel is positioned within the flow indicator housing;
   the one-way inhalation valve configured to allow a flow of aerosol to pass from the interior space of the chamber housing to the mouthpiece but not to the atmosphere during inhalation,
   the one-way exhalation valve configured to allow a flow of exhaled air to pass from the mouthpiece to the atmosphere but not to the interior space of the chamber housing during exhalation.

2. The aerosol inhalation spacer according to claim 1, wherein the inhalation valve comprises a one-way inhalation flap valve.

3. The aerosol inhalation spacer according to claim 1, wherein the exhalation valve comprises a one-way exhalation flap valve.

4. The aerosol inhalation spacer according to claim 1, wherein the exhalation valve and the chamber housing are configured to direct exhaled air to vent away from the patient's face.

5. The aerosol inhalation spacer according to claim 1, further comprising at least one air vent disposed in communication with the exhalation valve.

6. The aerosol inhalation spacer according to claim 5, wherein the at least one air vent is located on an exterior sidewall of the chamber housing.

7. The aerosol inhalation spacer according to claim 6, wherein the mouthpiece further comprises a shroud portion configured to cover a side of the output end of the chamber housing and at least partially cover the at least one air vent.

8. The aerosol inhalation spacer according to claim 5, wherein the at least one air vent is located on the mouthpiece.

9. The aerosol inhalation spacer according to claim 8, further comprising a plurality of air vents,
   wherein the plurality of air vents are disposed around a circumference of the mouthpiece,
   wherein at least one of the plurality of air vents is disposed on one side of the mouthpiece, and
   wherein at least one of the plurality of air vents is disposed on an opposing side of the mouthpiece.

10. The aerosol inhalation spacer according to claim 1, wherein the pinwheel is configured to spin in response to an inhalation airflow, the pinwheel configured to visibly indicate the inhalation flow rate to the patient via the transparent chamber housing.

11. The aerosol inhalation spacer according to claim 1, wherein the whistle is configured to make an audible sound if the inhalation flow rate exceeds a predetermined level.

12. The aerosol inhalation spacer according to claim 1, wherein the inhaler adapter comprises an inhaler port having a flexible cover.

13. The aerosol inhalation spacer according to claim 12, wherein the flexible cover comprises an elastomeric wing.

14. An aerosol inhalation device for use with an inhaler, the device comprising:
   an aerosol holding chamber including a housing defining a distal end, a proximal end, and an interior space between the distal and proximal ends configured to hold an administered dose of aerosol from the inhaler;
   a mouthpiece coupled to the distal end of the housing;
   an adapter coupled to the proximal end of the housing, the adapter configured to removably couple to the inhaler;
   a flow baffle positioned on the distal end of the housing, the flow baffle having a convex surface that extends away from the distal end of the housing and towards the proximal end of the housing;

a flow indicator connected to the adapter and extending into the interior space of the chamber housing, the flow indicator configured to indicate an inhalation flow rate to the patient, the flow indicator including a rotatable pinwheel that is visible to the patient and is coupled to a whistle, such that an inhalation flowpath is directed to the rotatable pinwheel through the whistle, wherein the flow indicator includes a flow indicator housing, the rotatable pinwheel and the whistle coupled to the flow indicator housing, and wherein the rotatable pinwheel is positioned within the flow indicator housing; and a valve member operable to allow a flow of aerosol to pass from the interior space of the chamber housing to the mouthpiece but not to the atmosphere during inhalation, and further operable to allow a flow of exhaled air to pass from the mouthpiece to the atmosphere but not to the interior space of the chamber housing during exhalation.

15. The aerosol inhalation device of claim 14, wherein the convex surface of the flow baffle is aligned with a central axis of the aerosol holding chamber;

wherein the flow baffle is aligned with a discharge orifice of the distal end of the housing to partially block the discharge orifice;

wherein the flow baffle is configured to act as an impact surface for aerosol projected by the inhaler; and wherein the flow baffle is configured to reduce a downstream flow velocity of the aerosol.

16. The aerosol inhalation device of claim 14, wherein the convex surface of the flow baffle is aligned with a central axis of the aerosol holding chamber;

wherein the flow baffle is aligned with a discharge orifice of the distal end of the housing to partially block the discharge orifice; and wherein during inhalation, the aerosol within the chamber is configured to flow along a first flow path and a second flow path, the first flow path extending from the chamber above the flow baffle, and through the discharge orifice, and the second flow path extending from the chamber below the flow baffle, and through the discharge orifice.

17. A method of administering a dose of aerosol medication to a patient from a metered-dose inhaler, the method comprising:

providing an aerosol inhalation spacer comprising:

an aerosol holding chamber including a housing defining a distal end, a proximal end, and an interior space between the distal and proximal ends configured to hold an administered dose of aerosol from the inhaler;

a mouthpiece coupled to the distal end of the housing;

an adapter coupled to the proximal end of the housing, the adapter configured to removably couple to the inhaler;

a flow baffle positioned the distal end of the housing, the flow baffle having a convex surface that extends away from the distal end of the housing and towards the proximal end of the housing;

a flow indicator connected to the adapter and extending into the interior space of the chamber housing, the flow indicator configured to indicate an inhalation flow rate to the patient, the flow indicator including a rotatable pinwheel that is visible to a user and is coupled to a whistle, such that an inhalation flowpath is directed to the rotatable pinwheel through the whistle, wherein the flow indicator includes a flow indicator housing, the rotatable pinwheel and the whistle coupled to the flow indicator housing, and wherein the rotatable pinwheel is positioned within the flow indicator housing; and a valve member operable to allow a flow of aerosol to pass from the interior space of the chamber housing to the mouthpiece but not to the atmosphere during inhalation, and further operable to allow a flow of exhaled air to pass from the mouthpiece to the atmosphere but not to the interior space of the chamber housing during exhalation;

mounting the metered-dose inhaler to the holding chamber by inserting a dispensing portion of the inhaler through an aperture in the adapter;

dispensing a dose of the aerosol medication from the metered-dose inhaler into the interior space of the holding chamber to mix with air in the chamber for inhalation by a patient through the mouthpiece.

\* \* \* \* \*